US009359639B2

(12) United States Patent
Li et al.

(10) Patent No.: US 9,359,639 B2
(45) Date of Patent: Jun. 7, 2016

(54) METHOD FOR THE DETECTION OF MULTIPLE SINGLE NUCLEOTIDE VARIATIONS OR SINGLE NUCLEOTIDE POLYMORPHISMS IN A SINGLE TUBE

(75) Inventors: Qingge Li, Xiamen (CN); Qiuying Huang, Xiamen (CN); Xiaobo Wang, Xiamen (CN)

(73) Assignee: XIAMEN UNIVERSITY, Xiamen (CN)

( * ) Notice: Subject to any disclaimer, the term of this patent is extended or adjusted under 35 U.S.C. 154(b) by 0 days.

(21) Appl. No.: 13/322,664

(22) PCT Filed: May 26, 2010

(86) PCT No.: PCT/CN2010/000752
§ 371 (c)(1),
(2), (4) Date: Dec. 30, 2011

(87) PCT Pub. No.: WO2010/135916
PCT Pub. Date: Dec. 2, 2010

(65) Prior Publication Data
US 2012/0141995 A1 Jun. 7, 2012

(30) Foreign Application Priority Data

May 26, 2009 (CN) .......................... 2009 1 0143479
May 26, 2009 (CN) .......................... 2009 1 0143480

(51) Int. Cl.
| | | |
|---|---|---|
| *C12P 19/34* | (2006.01) | |
| *C12Q 1/68* | (2006.01) | |
| *C07H 21/02* | (2006.01) | |
| *C07H 21/04* | (2006.01) | |
| *C07H 21/00* | (2006.01) | |

(52) U.S. Cl.
CPC ............ *C12Q 1/6827* (2013.01); *C12Q 1/6858* (2013.01)

(58) Field of Classification Search
USPC .............. 435/6.1, 6.11, 6.12, 91.1, 91.2, 183; 436/94, 501; 536/23.1, 24.3, 24.33, 536/25.3
See application file for complete search history.

(56) References Cited

FOREIGN PATENT DOCUMENTS

| CN | 1625603 A | 6/2005 |
|---|---|---|
| EP | 1295941 A1 | 3/2003 |
| WO | 02/083952 A1 | 10/2002 |
| WO | 2009/126678 A2 | 10/2009 |

OTHER PUBLICATIONS

Jiang, "System for Detecting Single Nucleotide Polymorphisms Based on Hybridization Probes," Practical Preventive Medicine, 2007, vol. 14, No. 1, pp. 1-3 (in English and Chinese).
International Search Report for PCT/CN10/000752 mailed Sep. 2, 2010.
Meng et al., "Fidelity genotyping of point mutation by enhanced melting point difference using DNA ligase," Talanta, vol. 73, No. 1, Jul. 26, 2007, pp. 23-29.
Supplementary European Search Report for EP Application No. 10 77 9998, dated Nov. 16, 2012.
Nicklas & Buel, "A Real-Time Multiplex SNP Melting Assay to Discriminate Individuals," J Forensic Sci., Nov. 2008, vol. 53, No. 6, pp. 1316-1324.

*Primary Examiner* — Frank Lu
(74) *Attorney, Agent, or Firm* — Banner & Witcoff, Ltd.

(57) ABSTRACT

The present invention discloses a method for detecting multiple single nucleotide variations or polymorphisms in a single reaction tube, and the oligonucleotide, the probe, the set of probes, the kit used, as well as the use thereof. Specifically, it relates to a method for identifying the genotype of multiple single nucleotide variation or SNP sites from the melting temperature of a kind of artificial melting temperature tag sequence (AMTS) and the type of fluorescence labels.

4 Claims, 6 Drawing Sheets

SEQUENCE LISTING

```
<160> NUMBER OF SEQ ID NOS: 42

<210> SEQ ID NO 1
<211> LENGTH: 29
<212> TYPE: DNA
<213> ORGANISM: Artificial Sequence
<220> FEATURE:
<223> OTHER INFORMATION: probe

<400> SEQUENCE: 1
ccggtccttc atcgctcagc cttcaccgg                                      29

<210> SEQ ID NO 2
<211> LENGTH: 37
<212> TYPE: DNA
<213> ORGANISM: Homo sapiens

<400> SEQUENCE: 2
tttttccggt gaaggctgag cgatgaagga cctttttt                             37

<210> SEQ ID NO 3
<211> LENGTH: 37
<212> TYPE: DNA
<213> ORGANISM: Homo sapiens

<400> SEQUENCE: 3
tttttccggt gatggctgag cgatgaagga cctttttt                             37

<210> SEQ ID NO 4
<211> LENGTH: 37
<212> TYPE: DNA
<213> ORGANISM: Homo sapiens

<400> SEQUENCE: 4
tttttccggt gatggctgag cgattaagga cctttttt                             37
```

```
<210> SEQ ID NO 5
<211> LENGTH: 37
<212> TYPE: DNA
<213> ORGANISM: Homo sapiens

<400> SEQUENCE: 5
tttttccggt gaagcctgag cgattaagga ccttttt                              37

<210> SEQ ID NO 6
<211> LENGTH: 37
<212> TYPE: DNA
<213> ORGANISM: Homo sapiens

<400> SEQUENCE: 6
tttttccggt gatggctgac cgatcaagga ccttttt                              37

<210> SEQ ID NO 7
<211> LENGTH: 37
<212> TYPE: DNA
<213> ORGANISM: Homo sapiens

<400> SEQUENCE: 7
tttttccggt caaggttgag ttatgaagga ccttttt                              37

<210> SEQ ID NO 8
<211> LENGTH: 37
<212> TYPE: DNA
<213> ORGANISM: Homo sapiens

<400> SEQUENCE: 8
tttttccggt gtaggttcag agatcaagga ccttttt                              37

<210> SEQ ID NO 9
<211> LENGTH: 37
<212> TYPE: DNA
<213> ORGANISM: Homo sapiens

<400> SEQUENCE: 9
tttttccggt gtaggttgag acatcaagga ccttttt                              37

<210> SEQ ID NO 10
<211> LENGTH: 79
<212> TYPE: DNA
<213> ORGANISM: Homo sapiens

<400> SEQUENCE: 10
tgggttccct aagggttgga cctcactcag ttcagttata tggatgatgt ggctgttttc     60
cttttgtgat tccacttcc                                                  79

<210> SEQ ID NO 11
<211> LENGTH: 80
<212> TYPE: DNA
<213> ORGANISM: Homo sapiens

<400> SEQUENCE: 11
tgggttccct aagggttgga cctcactcag ttcagctata tggatgatgt ggcctgtttt     60 cctttttgtga ttccacttct                                                80

<210> SEQ ID NO 12
<211> LENGTH: 54
<212> TYPE: DNA
<213> ORGANISM: Homo sapiens
```

<400> SEQUENCE: 12
gtgtgaagca agcagtgctt gttttaatca gtctagattg gatcttgctg gcac    54

<210> SEQ ID NO 13
<211> LENGTH: 20
<212> TYPE: DNA
<213> ORGANISM: Homo sapiens

<400> SEQUENCE: 13
tgggttccct aagggttgga    20

<210> SEQ ID NO 14
<211> LENGTH: 23
<212> TYPE: DNA
<213> ORGANISM: Homo sapiens

<400> SEQUENCE: 14
gtgccagcaa gatccaatct aga    23

<210> SEQ ID NO 15
<211> LENGTH: 26
<212> TYPE: DNA
<213> ORGANISM: Homo sapiens

<400> SEQUENCE: 15
ttttcagtta tatggatgat gtggbh    26

<210> SEQ ID NO 16
<211> LENGTH: 84
<212> TYPE: DNA
<213> ORGANISM: Homo sapiens

<400> SEQUENCE: 16
tgggttccct aagggttgga cgtcactcag ggtccttaat cgctcagcca tcaccggctg    60
ttttcctttt gtgattccac ttcc    84

<210> SEQ ID NO 17
<211> LENGTH: 58
<212> TYPE: DNA
<213> ORGANISM: Homo sapiens

<400> SEQUENCE: 17
tgggttccct aagggttgga cgtcactcag cctgttttcc ttttgtgatt ccacttct    58

<210> SEQ ID NO 18
<211> LENGTH: 54
<212> TYPE: DNA
<213> ORGANISM: Homo sapiens

<400> SEQUENCE: 18
gtgtgaagca agcagtgctt gttttaatca gtctagattg gatcttgctg gcac    54

<210> SEQ ID NO 19
<211> LENGTH: 78
<212> TYPE: DNA
<213> ORGANISM: Homo sapiens

<400> SEQUENCE: 19
tgggttccct aagggttgga cgtcactcag ggtccttcat cgctcagcct tcaccggcct    60
cccacaccag tttctcca    78

```
<210> SEQ ID NO 20
<211> LENGTH: 51
<212> TYPE: DNA
<213> ORGANISM: Homo sapiens

<400> SEQUENCE: 20
gagtggaaag actttcatct cgcactggtc tagattggat cttgctggca c          51

<210> SEQ ID NO 21
<211> LENGTH: 84
<212> TYPE: DNA
<213> ORGANISM: Homo sapiens

<400> SEQUENCE: 21
tgggttccct aagggttgga cgtcactcag ggtccttaat cgctcagcca tcaccggctg  60
ttttcctttt gtgattccac ttcc                                        84

<210> SEQ ID NO 22
<211> LENGTH: 54
<212> TYPE: DNA
<213> ORGANISM: Homo sapiens

<400> SEQUENCE: 22
gtgtgaagca agcagtgctt gttttaatca gtctagattg gatcttgctg gcac        54

<210> SEQ ID NO 23
<211> LENGTH: 79
<212> TYPE: DNA
<213> ORGANISM: Homo sapiens

<400> SEQUENCE: 23
tgggttccct aagggttgga cgtcactcag ggtccttgat cggtcagcca tcaccggctc  60
accaccagaa atcagggca                                              79

<210> SEQ ID NO 24
<211> LENGTH: 45
<212> TYPE: DNA
<213> ORGANISM: Homo sapiens

<400> SEQUENCE: 24
tgatggacct gaagcggtcc cgtctagatt ggatcttgct ggcac                  45

<210> SEQ ID NO 25
<211> LENGTH: 78
<212> TYPE: DNA
<213> ORGANISM: Homo sapiens

<400> SEQUENCE: 25
tgggttccct aagggttgga cgtcactcag ggtccttcat cgctcagcct tcaccggcct  60
cccacaccag tttctcca                                               78

<210> SEQ ID NO 26
<211> LENGTH: 78
<212> TYPE: DNA
<213> ORGANISM: Homo sapiens

<400> SEQUENCE: 26
tgggttccct aagggttgga cgtcactcag ggtccttcat cgctcagcca tcaccggcct  60
cccacaccag tttctccg                                               78
```

<210> SEQ ID NO 27
<211> LENGTH: 51
<212> TYPE: DNA
<213> ORGANISM: Homo sapiens

<400> SEQUENCE: 27
gagtggaaag actttcatct cgcactggtc tagattggat cttgctggca c           51

<210> SEQ ID NO 28
<211> LENGTH: 84
<212> TYPE: DNA
<213> ORGANISM: Homo sapiens

<400> SEQUENCE: 28
tgggttccct aagggttgga cgtcactcag ggtccttaat cgctcagcca tcaccggctg     60
ttttcctttt gtgattccac ttcc                                            84

<210> SEQ ID NO 29
<211> LENGTH: 85
<212> TYPE: DNA
<213> ORGANISM: Homo sapiens

<400> SEQUENCE: 29
tgggttccct aagggttgga cgtcactcag ggtccttaat cgctcaggct tcaccggcct     60
gttttccttt tgtgattcca cttct                                           85

<210> SEQ ID NO 30
<211> LENGTH: 54
<212> TYPE: DNA
<213> ORGANISM: Homo sapiens

<400> SEQUENCE: 30
gtgtgaagca agcagtgctt gttttaatca gtctagattg gatcttgctg gcac           54

<210> SEQ ID NO 31
<211> LENGTH: 79
<212> TYPE: DNA
<213> ORGANISM: Homo sapiens

<400> SEQUENCE: 31
tgggttccct aagggttgga cgtcactcag ggtccttgat cggtcagcca tcaccggctc     60
accaccagaa atcagggca                                                  79

<210> SEQ ID NO 32
<211> LENGTH: 79
<212> TYPE: DNA
<213> ORGANISM: Homo sapiens

<400> SEQUENCE: 32
tgggttccct aagggttgga cgtcactcag ggtccttcat aactcaacct tgaccggctc     60
accaccagaa atcagggct                                                  79

<210> SEQ ID NO 33
<211> LENGTH: 45
<212> TYPE: DNA
<213> ORGANISM: Homo sapiens

<400> SEQUENCE: 33
tgatggacct gaagcggtcc cgtctagatt ggatcttgct ggcac                     45

```
<210> SEQ ID NO 34
<211> LENGTH: 84
<212> TYPE: DNA
<213> ORGANISM: Homo sapiens

<400> SEQUENCE: 34
tgggttccct aagggttgga cgtcactcag ggtccttgat ctctgaacct acaccggcag    60
tctgcaacaa gatcttgtag ggac                                          84

<210> SEQ ID NO 35
<211> LENGTH: 84
<212> TYPE: DNA
<213> ORGANISM: Homo sapiens

<400> SEQUENCE: 35
tgggttccct aagggttgga cgtcactcag ggtccttgtt ctctgaacct tcaccggcag    60
tctgcaacaa gatcttgtag ggat                                          84

<210> SEQ ID NO 36
<211> LENGTH: 56
<212> TYPE: DNA
<213> ORGANISM: Homo sapiens

<400> SEQUENCE: 36
gctatcgctg gctattaggt gatcacagtt ctgtctagat tggatcttgc tggcac       56

<210> SEQ ID NO 37
<211> LENGTH: 78
<212> TYPE: DNA
<213> ORGANISM: Homo sapiens

<400> SEQUENCE: 37
tgggttccct aagggttgga cgtcactcag ggtccttcat cgctcagcct tcaccggcct    60
cccacaccag tttctcca                                                 78

<210> SEQ ID NO 38
<211> LENGTH: 78
<212> TYPE: DNA
<213> ORGANISM: Homo sapiens

<400> SEQUENCE: 38
tgggttccct aagggttgga cgtcactcag ggtccttcat cgctcagcca tcaccggcct    60
cccacaccag tttctccg                                                 78

<210> SEQ ID NO 39
<211> LENGTH: 51
<212> TYPE: DNA
<213> ORGANISM: Homo sapiens

<400> SEQUENCE: 39
gagtggaaag actttcatct cgcactggtc tagattggat cttgctggca c             51

<210> SEQ ID NO 40
<211> LENGTH: 79
<212> TYPE: DNA
<213> ORGANISM: Homo sapiens

<400> SEQUENCE: 40
tgggttccct aagggttgga cctcactcag ttcagttata tggatgatgt ggctgttttc    60
cttttgtgat tccacttcc                                                79
```

```
-continued

<210> SEQ ID NO 41
<211> LENGTH: 80
<212> TYPE: DNA
<213> ORGANISM: Homo sapiens

<400> SEQUENCE: 41
tgggttccct aagggttgga cctcactcag ttcagctata tggatgatgt ggcctgtttt      60 cctttgtga ttccacttct                                                   80

<210> SEQ ID NO 42
<211> LENGTH: 54
<212> TYPE: DNA
<213> ORGANISM: Homo sapiens

<400> SEQUENCE: 42
gtgtgaagca agcagtgctt gttttaatca gtctagattg gatcttgctg gcac            54
```

METHOD FOR THE DETECTION OF MULTIPLE SINGLE NUCLEOTIDE VARIATIONS OR SINGLE NUCLEOTIDE POLYMORPHISMS IN A SINGLE TUBE

This application incorporates by reference the content of a 7.5 kb text file created on Nov. 28,2011 and named "PCTCN2010000752sequencelisting.txt, "which is the sequence listing for this application.

The present invention claims priority of the Chinese patent applications No. 2009 1014 3480.6 and No. 2009 1014 3479.3 filed on May 26, 2009 in the name of Xiamen University, these two priority applications are incorporated herein in their entirety by reference, as if the entire contents thereof are explicitly described in the present application.

FIELD OF THE INVENTION

The present invention relates to a method for detecting multiple single nucleotide variations or polymorphisms in a single tube, in particular, a method for recognizing the genotype of multiple single nucleotide polymorphisms (or SNPs) through the artificial melting temperature tag sequence and the type of a fluorescent label.

BACKGROUND ART

Variation or polymorphism in a genome commonly exists in biological organisms; it mainly refers to differences of genomic sequences among different species or among different individuals of the same species, including differences of sequences in the gene coding region and non-coding region. Variation or polymorphism of DNA reflects the evolutionary process of the establishment, selection, migration, recombination and mating system of a species, laying the foundation of the rich and colorful biological world, and it serves as the basis of biodiversity. The most common and simple form of DNA variation or polymorphism is the variation or polymorphism of a single nucleotide in the genome, namely single nucleotide variation or polymorphism. Single nucleotide polymorphism (or SNP) is the most commonly seen form of variation in human genomic DNA sequence, and is one important genetic marker, which is believed to be associated with an individual's phenotypic differences, susceptibility to a disease, and response or resistance to a drug, etc. Such a variation or polymorphism also widely exists in other species, and has important biological functions as well. Thus, the detection of single nucleotide variation or polymorphism is of great significance.

There are many methods useful for detecting and genotyping single nucleotide variation (or SNP) (Ragoussis, J. Annu Rev Genomics Hum Genet, 2009, 10, 117-133), such as restrictive fragment length polymorphism, single strand conformation polymorphism analysis, allele specific oligonucleotide probe hybridization, denatured gradient gel electrophoresis, allele specific amplification system, oligonucleotide ligation analysis, reverse dot blot, denaturing high performance liquid chromatography, mass spectrometry, gene chips, pyrosequencing, gene sequencing and so on. Since all these technologies require post PCR manipulations, it is easy to cause contamination of the amplification products. The analysis procedure is relatively complicated and time-consuming, and cannot meet the clinical requirement of being fast and convenient.

Real-time PCR refers to carrying out amplification and detection simultaneously, wherein the amplification process is indicated through detecting changes of fluorescence signals in amplification cycles. As an important homogenous detection technology, recently, real-time PCR has been widely used in the detection and genotyping of single nucleotide variation or SNP. Currently, based on whether a fluorescent probe is used, real-time PCR can be divided into the probe-based type and the non-probe-based type. Since the probe-based real-time PCR has probe that can increase the specificity in recognizing a template, it is more specific than the detection results from the non-probe-based real-time PCR. The probe-based real-time PCR can also achieve the aim of detecting multiple target sequences by labeling different target-specific probes with different fluorescent groups. Thus, the probe-based real-time PCR is relatively more commonly used. There are many types of probes used in the probe-based real-time PCR, including TaqMan™ probe (Livak, K. J. Genetic Analysis, 1999, 14, 143-149.), TaqMan-MGB™ probe (Afonina, I. A. et al, Biotechniques, 2002, 32, 4, 940-944, 946-949), molecular beacons (Tyagi, S. et al, Nature Biotechnology, 1998, 16, 49-53), displacing probe (Li, Q., et al, Nucleic Acids Research, 2002, 30, E5.), scorpions (Whitcombe, D. et al, Nature Biotechnology, 1999, 17, 804-807), amplifier primer (Nazarenko, I. A., et al, Nucleic Acids Research, 1997, 25, 1516-1521) etc. When these probes are used in the detection of single nucleotide variation or SNP, the most often used mode is that two allele-specific probes labeled with different fluorescent groups are used to detect a single nucleotide variation or SNP, as described by Ruan L et al. (Ruan, L., et al. Transfusion. 2007, 47(9):1637-42), wherein they accomplished the detection of 6 single nucleotide variations or SNPs in 3 reaction tubes. Restricted by the number of detection channel of the existing real-time PCR machines, using said method, at most 3 single nucleotide variations or SNPs could be detected simultaneously in a single tube. Therefore, although real-time PCR can meet the clinical requirements of being fast and convenient, however, the number of single nucleotide variations or SNPs detected in a single tube is limited, and it often needs several tubes to detect multiple single nucleotide variations or SNPs, which fails to meet the high throughput requirement in clinical testing, and the cost is relatively high.

Another approach of detecting single nucleotide variation or SNP is using melting curve analysis after real-time PCR, wherein the genotype of a single nucleotide variation or SNP is identified by differences of the melting temperature when a probe hybridizes with different targets. Using this detection approach, genotyping of one single nucleotide variation or SNP can be achieved using one fluorescent probe. In comparison with the real-time PCR approach discussed above (wherein the genotype of one single nucleotide variation or SNP is detected by using two probes labeled with different colors), the number of single nucleotide variations or SNPs detected using this method in a single tube is doubled. As described by Nicklas J A et al. (Nicklas, J. A., et al. Journal of Forensic Sciences, 2008, 53(6):1316-24), wherein they achieved with a single tube the detection of the genotype of 6 single nucleotide variations or SNPs in a 6 color real-time PCR machine, using melting curve analysis by adjacent probes. However, for detecting more single nucleotide variations or SNPs, this method still needs more reaction tubes, and thus still cannot meet the clinical requirement of high throughput detection. In addition, because only one or few single nucleotide variations or SNPs can be detected using one fluorescent probe, the cost is still relatively high.

DETAILED DESCRIPTION OF THE INVENTION

To overcome those disadvantages such as complicated manipulation, taking a long time, easy to be contaminated and having a throughput unable to meet the clinical requirements existing in the prior art, the present invention provides a method for detecting the genotype of multiple single nucleotide variations or polymorphism sites in a single reaction tube. Preferably, in the technical solution thereof, the genotype of a single nucleotide variation (or SNP) is labeled with a specific artificial melting temperature tag sequence (AMTS) by examining the differences of peaks (melting temperature) of the melting curves derived from hybridization of a fluorescent probe with multiple different AMTS, the genotype of various single nucleotide variation (or SNP) sites can be distinguished, thereby achieving the aim of simultaneously detecting the genotype of multiple single nucleotide variations (or SNPs) in a single tube using several probes labeled with different fluorescent groups.

In one aspect, the present invention provides a probe, a set of probes or a kit for detecting single nucleotide variation or gene polymorphism, preferably for detecting multiple single nucleotide variations or gene polymorphisms in a single tube, as well as the use thereof in the detection of single nucleotide variation or gene polymorphism, preferably in the detection of multiple single nucleotide variations or gene polymorphisms in a single tube.

In another aspect, the present invention provides a method for detecting single nucleotide variation or gene polymorphism, preferably for detecting multiple single nucleotide variations or gene polymorphisms in a single tube. Specifically, the present invention relates to a method for identifying the genotype of multiple single nucleotide variation (or SNP) sites using the melting temperature of artificial melting temperature tag sequences (AMTS). Preferably said method comprises, first of all, labeling with AMTS the single nucleotide variation (or SNP) through the hybridization of a hybridization probe and a ligation reaction; then, PCR amplification is performed and after the amplification, melting curve analysis is performed to detect the fluorescent probe, based on the differences of peak value (melting temperature) of the melting curves, the genotype of various single nucleotide variation (or SNP) sites is distinguished, thereby achieving the aim of simultaneously detecting the genotype of multiple single nucleotide variations (or SNPs) in a single tube.

One preferred specific embodiment of the present invention is as follows:

Step 1: labeling a single nucleotide variation (or SNP) with AMTS: the designed AMTS is added to the 5' end of the left hybridization probe in the ligation reaction, the base in the 3' end of the left hybridization probe is the site of the single nucleotide variation (or SNP) to be detected; after the addition of the AMTS, the sequence of the left hybridization probe includes four parts (FIG. 1), which in the order of from 5' end to 3' end are: universal upstream primer binding sequence, an optional spacer sequence, the AMTS sequence, a template hybridization sequence. The corresponding right hybridization probe of the ligation reaction includes two parts, which in the order from 5' end to 3' end are: template binding sequence and a downstream primer binding sequence (FIG. 1). A spacer sequence may be (but not necessarily) comprised between different parts.

Step 2, the realization of AMTS labeling: by a specific ligation reaction using a nucleic acid ligase, the left hybridization probe is ligated with the right hybridization probe to form a complete single-stranded nucleic acid, and thereby achieving the conversion from the genotype of a single nucleotide variation (or SNP) to be detected into the corresponding AMTS melting temperature, accomplishing the AMTS labeling of a single nucleotide variation (or SNP).

Step 3, detecting a single nucleotide variation (or SNP) site: after finishing with the labeling described above, PCR amplifying the above ligation product with a pair of primers, the PCR reaction system comprises a probe hybridizing with the AMTS; after PCR, melting curve analysis is performed, information concerning the genotype of the single nucleotide variation (or SNP) to be detected can be obtained according to the peak of a melting curve.

Said AMTS is a predesigned sequence of oligonucleotide, upon hybridizing with a detection fluorescent probe, said sequence shows a specific melting temperature, which could be detected by a fluorescent probe, preferably in the form of a melting curve.

Said labeling the genotype of a single nucleotide variation (or SNP) using AMTS generally is the conversion of the genotype of a single nucleotide variation (or SNP) into the peak (melting temperature) of a melting curve that is detectable, this conversion is achieved preferably with a ligation reaction catalyzed by a nucleic acid ligase.

One design approach of said left hybridization probe may be: designing two allele-specific left hybridization probes for two homozygous genotypes of a single nucleotide variation (or SNP) site, which are respectively labeled with two AMTSs that are able to be detected by one common fluorescent probe. This method, based on the genotype of a single nucleotide variation (or SNP), may provide three different melting curve peaks, which are two homozygous and one heterozygous, respectively, and they correspond to two single peaks of different melting temperatures and one heterozygous double-peak. This approach of designing a hybridization probe is characterized by that for the detection of each single nucleotide variation (or SNP) site, two allele-specific left hybridization probes need to be designed, and two AMTSs need to be used, while only one fluorescent probe is required.

Another design approach of said left hybridization probe may be: two allele-specific left probes are designed for two homozygous genotypes of a single nucleotide variation (or SNP) site, the probes are labeled respectively with two AMTS labels that may have the same or similar melting temperatures while having significantly different sequences, carrying out the detection using their corresponding fluorescent probes labeled with different fluorescence, so that the melting temperatures of the two genotypes to be detected are identical or similar but the types of fluorescence are different; in this way, three different melting curve peaks may be provided based on the genotype of the single nucleotide variation (or SNP), which respectively are two homozygous and one heterozygous, corresponding to two single peaks of similar or identical melting temperatures but with different fluorescence labels, and one heterozygous double peak. This approach of designing a hybridization probe is characterized by that for the detection of each single nucleotide variation (or SNP) site, two allele-specific left hybridization probes need to be designed, two AMTS and two fluorescent probes labeled with different fluorescence need to be used.

Another design approach of said left hybridization probe may be: only one left hybridization probe is designed for a single nucleotide variation (or SNP) site, corresponding to one homozygous type and it is labeled with one AMTS label. In this way, three different melting curve peaks are provided as well based on the genotype of the single nucleotide variation (or SNP), wherein the high single peak corresponds to the matched homozygous type, the low single peak corresponds to the heterozygous genotype, and the absence of a peak corresponds to the other homozygous genotype. This approach of designing a hybridization probe is characterized by that for the detection of each single nucleotide variation (or SNP) site, only one left hybridization probe needs to be designed and only two (or one) AMTS need to be used, while the identification of the genotype of a single nucleotide variation (or SNP) depends on the height of the melting curve peak. Comparing to the designs described above, with this design of left hybridization probe, one detection fluorescent probe can detect more single nucleotide variation (or SNP) sites.

Said detection fluorescent probe is preferably those fluorescent probes able to generate a characteristic melting curve peak and provide a melting temperature upon hybridizing with a target sequence, including but not limited to: a self-quenched probe (Chinese patent application No. 200910143480.6); a neighboring probe (Bernard, P. S., et al, American Journal of Pathology, 1998, 153, 1055-1061); tolerate type molecular beacon (Hiyam H. El-Hajj, et al, Journal of Clinical Microbiology, 2009, 47, 4, 1190-1198); an oligonucleotide probe only labeled with a fluorescent group, such as a HyBeacon probe (French, D. J., et al, Molecular and Cellular Probes, 2001. 15, 363-374); a probe dependent on the embedded dye, such as an unlabeled probe in combination with an embedded fluorescent dye, a fluorescence label in combination with an embedded fluorescent dye, a fluorescently labeled probe in combination with a fluorescence quenching dye (Gupta, A. P. et al, US patent application, US 2007/0020664 A1).

One characteristics of the present invention is, preferably, different genotypes of a single nucleotide variation (or SNP) may be labeled with a different AMTS, and these AMTS tags are detected using the same fluorescent probe, such a fluorescently labeled fluorescent probe can detect the genotype of multiple single nucleotide variations (or SNPs).

Another characteristics of the present invention is, preferably, the probes used may be labeled with various different fluorescence, a fluorescent probe labeled with one fluorescence can detect the genotype of multiple single nucleotide variations (or SNPs), thus the genotype of more single nucleotide variations (or SNPs) can be detected with a fluorescent probe labeled with multiple fluorescence.

Another characteristic of the present invention is, preferably, hybridization probes for multiple single nucleotide variation (or SNP) sites may be mixed to carry out hybridization and ligation reaction, in other words, hybridization and ligation reactions for multiple single nucleotide variation (or SNP) sites may be carried out simultaneously in the same reaction tube. After the ligation reaction, the reaction products are added into a PCR amplification system, and amplification is carried out using universal PCR upstream and downstream primers. In this reaction system, corresponding fluorescent probes for detecting different AMTS are present simultaneously. After PCR, with the melting curve analysis, single tube detection of the genotype of multiple single nucleotide variation (or SNP) sites can be achieved.

Another characteristic of the present invention is that preferably, the melting curve peak of a single nucleotide variation (or SNP) may be artificially adjusted; for example, the height of a peak in the melting curve may be adjusted by altering the amount of hybridization probes used or by introducing competitive probes. Using these approaches, the height of melting curve peaks of each single nucleotide variation (or SNP) detected by a fluorescent probe can be adjusted so that they are evened out for the convenience of determining the results, especially for determining results in detections depending on the height of the peaks.

In any aspect of the present invention, when appropriate, any of the single nucleotide variation mentioned is applicable to SNP, and SNP may also be applicable to single nucleotide variation. For the sake of clarity, when appropriate, "single nucleotide variation" and "SNP" may be used interchangeably.

In the present invention, an upstream PCR amplification primer specifically binds to an upstream primer binding sequence, and a downstream PCR amplification primer specifically binds to a downstream primer binding sequence; when the 3' end of a left probe and the 5' end of a right probe are ligated (preferably by a DNA ligase), the ligation product of the left probe and the right probe can be specifically amplified in a PCR amplification.

An upstream primer binding sequence is a sequence binding with an upstream PCR amplification primer (thus, the length and sequence of an upstream primer binding sequence is sufficient to specifically bind to an upstream PCR amplification primer, so that specific PCR amplification can be achieved), a universal upstream primer binding sequence is preferred, for example, the upstream primer binding sequences in a left probe are the same for the same single nucleotide variation site, alternatively, the upstream primer binding sequences in a left probe are the same for multiple (e.g. 2-30, 2-20, 2-16, 2-10, such as 2, 3, 4 or more) different single nucleotide variation sites, or that the upstream primer binding sequences are the same in the same PCR amplification reaction tube.

When using a universal upstream primer binding sequence, preferably, an upstream PCR amplification primer specifically binding to the universal upstream primer binding sequence is used.

Specific binding of an upstream PCR amplification primer and an upstream primer binding sequence preferably refers to, for example, the upstream PCR amplification primer does not bind to an unrelated upstream primer binding sequence, or that it does not bind to other unrelated sequences to amplify significantly.

A downstream primer binding sequence is a sequence binding with a downstream PCR amplification primer (thus, the length and sequence of a downstream primer binding sequence is sufficient to specifically bind to a downstream PCR amplification primer, so that specific PCR amplification can be achieved), a universal downstream primer binding sequence is preferred, for example, the downstream primer binding sequences in a left probe are the same for the same single nucleotide variation site, alternatively, the downstream primer binding sequences in a left probe are the same for multiple (e.g. 2-30, 2-20, 2-16, 2-10, such as 2, 3, 4 or more) different single nucleotide variation sites, or that the downstream primer binding sequences are the same in the same PCR amplification reaction tube.

A spacer sequence may be designed according to the general knowledge in the art, the preferred ones would not affect the specific binding and ligation of the left probe and the right probe with the target sequence, the specific PCR amplification and the melting curve analysis; the length of said space sequence may be, for example 1-30 nucleotide, preferably 1-20, 1-15, 2-10, 2-5, or 5-10 nucleotides.

An artificial melting temperature tag sequence is a fragment of oligonucleotide sequence, after the hybridization of said oligonucleotide with a detection fluorescent probe; it shows a specific melting temperature and/or type of fluorescence. The sequence of an artificial melting temperature tag sequence may be a sequence sufficient to achieve melting curve analysis after hybridizing with a detection fluorescent probe, to determine the specific melting temperature and the type of fluorescence thereof. The type of fluorescence is normally provided by a detection fluorescent probe. The length thereof may be, for example 10-100 nucleotide, such as 10-80, 10-50, 20-40, 20-50, 20-80, 30-40, 30-50 or 30-60 nucleotide. Generally, preferably, in one PCR amplification reaction tube, each artificial melting temperature tag sequence corresponds to a specific single nucleotide variation genotype, thus, each artificial melting temperature tag sequence corresponds to a specific left probe or the template hybridization sequence of a left probe, meaning that each left probe comprises a specific artificial melting temperature tag sequence. However, it is also possible that in one PCR amplification tube, one artificial melting temperature tag sequence corresponds to multiple single nucleotide variation genotypes. The artificial melting temperature tag sequence comprised in different PCR amplification reaction tubes may be identical or different.

Usually, the sequences of different AMTSs are different. Preferably, in one PCR amplification reaction tube, the AMTSs in the left probe have 1 or more (e.g. 2-16, 2-10, 2-8, such as 2, 3, 4, 8 or more) nucleotides difference but all are able to hybridize with the same detection fluorescent probe. However, the melting temperatures of the hybrid formed between the different AMTS and said same detection fluorescent probe are different (preferably with a difference of 1° C.-10° C., preferable with a difference of at least 1° C., 2° C., 3° C., 4° C., such as 1-4° C., 2-4° C., 2-5° C., 3-4° C.).

A template hybridization sequence of the left probe and the right probe is a sequence able to hybridize with a target sequence (template) to be tested, preferably, the hybridization is specific hybridization; preferably, it is completely complementary to the target sequence, but it may also comprise one or several (such as 1-5) mismatches. The length of a template hybridization sequence may be 5-200 nucleotides long, such as 5-100, 5-50, e.g. 5-30 nucleotides, 5-20, 5-15, or 5-10 nucleotides. The 3' end nucleotide in the template hybridization sequence of a left probe is identical or complementary to the specific allele of the single nucleotide variation to be detected.

A detection fluorescent probe is preferably a self-quenched fluorescent probe for the present invention.

Basic Principles of the Present Invention:

Allele-specific hybridization probes are designed for different single nucleotide variations (or SNPs), the hybridization probes include a left hybridization probe and a right hybridization probe (FIG. 1). A left hybridization probe comprises four parts, which from the 5' end to the 3' end are: a universal upstream primer binding sequence, a spacer sequence, an AMTS sequence, a template hybridization sequence; a right hybridization probe comprises two parts, which from the 5' end to the 3' end are: a template binding sequence and a downstream primer binding sequence. In this way, the genotype of a single nucleotide variation (or SNP) is labeled with a specific artificial melting temperature tag sequence (AMTS).

In a specific embodiment, the process of carrying out the present invention mainly comprises three stages: the hybridization and ligation of the hybridization probe, PCR amplification, and melting curve analysis. As shown in FIG. 2, after denaturation of a genomic DNA template, the hybridization probes hybridize with the genomic DNA template, if a left probe completely matches the template, then the left hybridization probe ligates with a right hybridization probe to form a complete single-stranded nucleic acid under the action of a nucleic acid ligase, and thereby achieving a conversion from the genotype of a single nucleotide variation (or SNP) to be detected into the corresponding AMTS's melting temperature, accomplishing the AMTS labeling of a single nucleotide variation (or SNP); the single-stranded nucleic acid is further amplified by a PCR reaction; finally, melting curve analysis is performed, wherein various genotypes of single nucleotide variation (or SNP) sites are differentiated by the differences of the melting curve peak values (melting temperature) formed through the hybridization of the detection fluorescent probe with different AMTS.

The method of using PCR-melting curve analysis to detect single nucleotide variation has been described in the Chinese patent application No. 2009 1014 3480.6 filed on May 26, 2009 in the name of Xiamen University, and the PCT application filed on May 26, 2010 by the same applicant claiming priority of the former.

During thermal denaturation of DNA, the temperature when 50% of the DNA denatures and melts is referred to as the melting temperature of double-stranded DNA, also called melting temperature or melting point (Tm). Under the precondition of a given solvent, the Tm of a double-stranded DNA is fixed. When the two strands of DNA are completely complementary, the double-stranded structure formed is relatively stable, and thus the temperature required for melting the two DNA strands is relatively high, resulting in a relatively high Tm; when the two DNA strands are not completely complementary, the double-stranded structure formed is relatively unstable, and thus the temperature required for melting the two DNA strands is relatively low, resulting in a relatively low Tm, in addition, the extent to which Tm decreases depends on the specific sequences that are not completely complementary.

Based on the above theory (but not limited to said theory), when a double-stranded structure is formed by the hybridization of a probe with a completely matched target, the double-stranded structure thus formed has a relatively high Tm; and when the probe hybridizes with a target that is not completely matched, the double-stranded structure formed has a relatively low Tm.

Therefore, if changes of Tm values can be detected, it would be possible to determine whether a variation exists in the target nucleic acid sequence, or even the specific type of said variation.

For a fluorescently labeled probe to be used in the detection of nucleic acid sequence variation, the following three conditions need to be met: 1) there must be a change in the fluorescence intensity before and after the hybridization of the probe with a target sequence; 2) the probe needs to stay intact during amplification in order to be used for the melting curve analysis after amplification; 3) the specificity of a probe cannot be too high, otherwise it would be difficult for a nucleic acid sequence having a variation to hybridize with the probe. The self quenched probe of the present invention can very well meet the three conditions described above. During melting curve analysis, the self-quenched probe hybridizes with a target sequence in the low temperature stage, when the probe and the target form a rigid and stable double-stranded structure. The fluorescent group is relatively far from the quenching group, so that the fluorescence emitted by the fluorescent group cannot be absorbed by the quenching group, making it possible to detect a very strong fluorescence signal; as the temperature increases, the probe gradually dissociates from the target, the dissociated probe is in a single-stranded, randomly coiled state, the labeled fluorescent group and the quenching group are close to each other, therefore the fluorescence emitted by the fluorescent group is absorbed by the quenching group, thereby generating only very weak fluorescence signal that can be detected. By detecting the fluorescence signal of a self-quenched probe during melting curve analysis, it would be possible to observe the hybridization and dissociation process between a probe and a target, and thereby forming a curve wherein the fluorescence intensity changes versus the temperature (namely a melting curve of the probe), and then by carrying out a derivation analysis of the melting curve, it would be possible to find the point where the biggest fluorescence change occurs, the corresponding temperature is the Tm of the probe. When a probe hybridizes with a completely matched target, the double-stranded structure formed has the highest Tm; and when a probe hybridizes with a target having various sequence variations, the double-stranded structure formed has a relatively low Tm, different types of variation may result in different Tm value. Thus, the method of self-quenched probe-based melting curve can be used to detect nucleic acid sequence variations.

Therefore, according to the present invention, by using a melting curve, it would be possible to obtain the melting temperature of a hybrid formed between a probe and the nucleic acid to be tested, based on the melting temperature, it would be possible to detect a variation in the nucleic acid to be tested.

Alternatively, preferably, according to the present invention, by using a melting curve, it would be possible to obtain the melting temperature of a hybrid formed between a probe and the nucleic acid to be tested and the melting temperature of a hybrid formed between a probe and a reference nucleic acid; according to the difference between these two melting temperatures, it would be possible to detect a variation in the nucleic acid to be tested. A reference nucleic acid may be the wild-type nucleic acid, for example.

Preferably, melting temperatures of the hybrids formed between a probe and the nucleic acid to be tested and between a probe and a reference nucleic acid are obtained in the same amplification reaction; alternatively, the melting temperatures of the hybrid formed between a probe and the nucleic acid to be tested and between a probe and a reference nucleic acid are obtained by using the same melting curve. More preferably, a single amplification reaction comprises at least one probe, at least one reference nucleic acid and multiple nucleic acids to be tested, thereby detecting multiple nucleic acid variations. More preferably, a single amplification reaction comprises multiple probes, at least one reference nucleic acid and multiple nucleic acids to be tested, thereby detecting multiple variations existing in multiple nucleic acids to be tested. Preferably, said multiple probes are labeled with different fluorescent groups. Said multiple probes may be at least 2, 3, 5, 7, 10, 15 or 20, and at most 10, 15, 20, 30 or 50 or more, such as 2-5, 2-10, 2-20, 5-10 or 5-20. Said multiple nucleic acids to be tested may be for example, at least 2, 3, 5, 7, 10, 15 or 20, and at most 10, 20, 50 or 100 or more, such as 2-10, 2-20, 2-50. Said multiple variations may be for example at least 2, 3, 5, 7, 10, 15, 20, 30, 50 or 100, and at most 10, 20, 50, 100 or 200 or more, such as 5-10, 5-20, 5-50, 10-50, 10-100 or 10-200.

More specifically, the melting curve analysis can be carried out according to the following embodiments:

1. A (self-quenched) nucleic acid probe for detecting target nucleic acid sequence variation (preferably by melting curve analysis), said probe being labeled with a fluorescent group and a quenching group, so that comparing to the situation where a target nucleic acid sequence is absent, fluorescence (or fluorescence intensity) increases when the probe hybridizes with the target nucleic acid sequence; and said probe may (but not necessarily) comprise a modification able to resist the exonuclease activity of a DNA polymerase,
    preferably, wherein:
    the 5' end of the probe is labeled with a fluorescent group and the 3' end of the probe is labeled with a quenching group; or alternatively, the 3' end of the probe is labeled with a fluorescent group and the 5' end is labeled with a quenching group;
    preferably, the sequence of the probe is or comprises the completely complementary sequence of a wild type or a variant target nucleic acid sequence; or, comparing to the completely complementary sequence of said wild-type or variant target nucleic acid sequence, the sequence of the probe comprises several (such as 1-10, 1-5, 1-4, 1-3, 1-2, 1 or 2) mismatches, for example, a sequence having one or more (such as 1-10, 1-5, 1-4, 1-3, 1-2, 1 or 2) conversion, transversion, insertion and/or deletion of a single base.

2. The probe of paragraph 1, wherein the fluorescent group comprises or is selected from the following labels: ALEX-350, FAM, VIC, TET, CAL Fluor® Gold 540, JOE, HEX, CAL Fluor® Orange 560, TAMRA, CAL Fluor® Red 590, ROX, CAL Fluor® Red 610, TEXAS RED, CAL Fluor® Red 635, Quasar 670, CY3, CY5, CY5.5 and/or Quasar 705.

3. The probe of paragraph 1, wherein said quenching group comprises or is selected from the following quenching agents: DABCYL, BHQ class quenching agent (e.g. BHQ-1 or BHQ-2), ECLIPSE and/or TAMRA.

4. The probe of paragraph 1, wherein said probe consists of unmodified bases.

5. The probe of paragraph 1, wherein said probe comprises bases able to increase or decrease the binding ability of the probe.

6. The probe of paragraph 5, wherein the base able to increase the binding ability of the probe includes a locked nucleic acid base.

7. The probe of paragraph 5, wherein the base able to decrease the binding ability of the probe includes a universal binding base I.

8. The probe of paragraph 1, wherein said probe comprises a modification able to resist the 5'→3' exonuclease activity of a DNA polymerase, preferably, the 5' end of said probe is able to resist the 5'→3' exonuclease activity of a DNA polymerase, said modification may be for example: modifying the linkage within bases in the 5' end (for example, within several bases, e.g. between the first and the second base), using a modified base derivative or adding a chemical functional group.

9. The probe of paragraph 8, wherein said modification of the linkage between bases in the 5' end includes employing a phosphorothioated linkage, a methylphosphonate linkage, a boranophosphated linkage or a peptide nucleic acid linkage.

10. The probe of paragraph 9, wherein said modification of the linkage between bases in the 5' end is employing a phosphorothioated linkage between the first base and the second base of the 5' end.

11. The probe of paragraph 8, wherein using a modified base derivative includes using a locked nucleic acid.

12. The probe of paragraph 1, wherein the probe comprises a modification able to resist the 3'→5' exonuclease activity of a DNA polymerase, preferably, the 3' end of the probe can resist the 3'→5' exonuclease activity of a DNA polymerase, said modification may be, for example: modifying the linkage between bases in the 3' end (e.g. between several bases, such as between the first and the second base), employing a modified base derivative or adding a chemical functional group.

13. The probe of paragraph 12, wherein said modification of the linkage between bases in the 3' end includes employing a phosphorothioated linkage, a methylphosphonate linkage, a boranophosphated linkage or a peptide nucleic acid linkage.

14. The probe of paragraph 13, wherein said modification of the linkage between bases in the 3' end is employing a phosphorothioated linkage within several bases (e.g. between the first base and the second base) of the 3' end.
15. The probe of paragraph 12, wherein using a modified base derivative includes using a locked nucleic acid.
16. The probe according to any one of paragraphs 1-15, wherein said probe is a linear probe, and the melting temperature thereof is not lower than the melting temperature of the primer used for amplification, wherein the length of said probe is 5-100 bases, such as 10-100, 10-50, 15-50, 20-50, 10-40 bases, or for example 10-20, 20-30, 30-40, 15-30, 20-40, 15-25 bases.
17. The probe of any one of paragraphs 1-15, wherein said probe is a hairpin structure probe, it may either be a natural hairpin structure probe or an artificial hairpin structure, but an artificial hairpin structure probe is preferred, namely an artificial hairpin structure formed by artificially adding bases unrelated to the target sequence at the terminal of the probe; the principle for adding such bases unrelated to the target sequence is that in the arm sequence of the so formed hairpin structure, part of or all of the bases are complementary to the target sequence, and thereby forming an arm with a length in general preferably of 2-15 bases, preferably 3-7 bases, more preferably 4-7 bases or 4-6 bases; wherein the melting temperature of the probe hybridized with the target sequence is not lower than the melting temperature of the primer used for amplification, and wherein the length of said probe is 5-100 bases, such as 10-100, 10-50, 15-50, 20-50, 10-40 bases, or for example 10-20, 20-30, 30-40, 15-30, 20-40, 15-25 bases.
18. A kit comprising one or more probe according to any one of paragraphs 1-16, wherein, when there are multiple probes, the fluorescent group on each probe is identical or different, optionally, said kit also comprises an amplification primer and/or nucleic acid polymerase and/or other components necessary for the amplification reaction; said kit may be used to perform nucleic acid amplification for the target gene to be tested, and to analyze target sequence variation with melting curve analysis.
19. A method for detecting the presence of a variation, such as a single nucleotide variation, or the type of a variation in a nucleic acid, comprising:
    (1) preparing a probe according to any of paragraph 1-17 directing to the nucleic acid where the detection of nucleic acid sequence variation is needed;
    (2) amplifying a fragment comprising the nucleic acid to be tested (e.g. by PCR), and adding said probe into the amplification reaction before, during or after the amplification (preferably before the amplification);
    (3) after the amplification, performing melting curve analysis for the amplification product comprising said probe obtained in step (2); determining whether the nucleic acid to be tested has a variation and, optionally, the possible type of variation, based on the corresponding melting temperature of the self-quenched probe (or the melting temperature of the hybrid formed between said probe and the nucleic acid sequence to be tested) or differences of said melting temperatures between different targets;
    preferably, the amplification product obtained in step (2) comprises sufficient intact probes for melting curve analysis;
    preferably, said amplification in step (2) is an asymmetric PCR, wherein one PCR amplification primer in the reaction mixture is relatively in excess, the strand produced with the elongation of said primer hybridizes with the probe;
    preferably, said amplification reaction comprises a reference nucleic acid or a wild type nucleic acid.
20. The method of paragraph 19, wherein said probe comprises a modification able to resist the exonuclease activity of a DNA polymerase, and/or said probe does not comprise a modification able to resist the exonuclease activity of a DNA polymerase, but the enzyme used for amplification does not have an exonuclease activity or has a sufficiently low exonuclease activity, so that the amplification product obtained in step (2) comprises sufficient intact probes for melting curve analysis.
21. The method of paragraph 19, wherein in step (2), said probe is added before amplification, said probe comprises or does not comprise a modification able to resist the exonuclease activity of a DNA polymerase, said amplification uses a thermophilic nucleic acid polymerase not having exonuclease activity or having very low exonuclease activity, to make sure that after the PCR reaction, there would still be enough intact probes of the pre-added probes for melting curve analysis.
22. A method for detecting the presence of a nucleic acid variation, such as a single nucleotide variation or for detecting the type of variation, comprising:
    (1) for one or more nucleic acid regions of the genome, each of which is to be tested for the presence of one or more allelic nucleic acid sequences variation having a target sequence variation, such as a single nucleotide variation in the target sequence, a number of probes according to any of paragraphs 1-17 or one or more kits of paragraph 18 comprising each of said probes are prepared to cover the nucleic acid segments to be tested, and said probes are added into the reaction system of (2) below before the PCR reaction begins;
    (2) amplifying in a PCR reaction system said one or more nucleic acid regions of the genome, each of which is to be tested for the presence of one or more sequence variations, such as a single nucleotide variation, in the target regions;
    (3) still in said reaction system, with gradual increase or decrease of the temperature, monitoring changes of fluorescence resulting from interactions between the probes prepared in step (1) and the to be tested nucleic acid sequences amplified in step (2), thereby simultaneously obtaining melting curves corresponding to each of said probes;
    (4) taking derivation for the melting curve obtained in step (3), and taking the negative derivative thereof (−dF/dT), thereby obtaining the melting temperatures corresponding to each of said probes; and
    (5) comparing the melting temperatures obtained in step (4) corresponding to each of the nucleic acid sequences to be tested and each of the probes, to analyze whether each of the nucleic acid sequences to be tested has a target sequence variation, such as a single nucleotide variation,
    wherein said single nucleotide variation may be conversion, transversion, insertion or deletion of a single base at one or more of the same or different positions in the nucleic acid sequence of the same gene locus among different individuals of the same species, and the one or more nucleic acid segments in said genome may be identical or different;

preferably, the amplification product obtained in step (2) comprises sufficient intact probes for melting curve analysis;

preferably, said amplification in step (2) is asymmetric PCR, wherein one PCR amplification primer in the reaction mixture is relatively in excess, the strand produced with the elongation of said primer hybridizes with the probe;

preferably, said amplification reaction comprises a reference nucleic acid or a wild-type nucleic acid.

23. The method of paragraph 22, wherein said probe comprises a modification able to resist the exonuclease activity of a DNA polymerase, and/or, said probe does not comprise a modification able to resist the exonuclease activity of a DNA polymerase, but said enzyme used for amplification does not have an exonuclease activity or only has a low exonuclease activity, so that the amplification product obtained in step (2) comprises sufficient intact probes for melting curve analysis.

24. Use of a probe according to any of paragraphs 1-17 or a kit according to paragraph 18 for detecting nucleic acid variation, such as the presence of a single nucleotide variation, or the type of variation, wherein for example, said single nucleotide variation may be conversion, transversion, insertion or deletion of a single base at one or more of the same or different positions in the nucleic acid sequence of the same gene locus among different individuals of the same species.

25. A method for detecting target sequence variation or the type of variation by nucleic acid amplification melting curve analysis using a self-quenched probe, wherein the sequence of the self-quenched probe used in said method comprises or is: the completely complementary sequence of a wild-type or variant target nucleic acid sequence; or a sequence having several (e.g. 1-10, 1-5, 1-3, 1-2, 1 or 2) mismatches, such as one or more (e.g. 1-10, 1-5, 1-3, 1-2, 1 or 2) single base conversion, transversion, insertion and/or deletion, compared to the completely complementary sequence of said wild-type or variant target nucleic acid sequence, said self-quenched probe is labeled with a fluorescent group and a quenching group, so that comparing to the situation where a target nucleic acid sequence is absent, fluorescence (or fluorescence intensity) increases when said probe hybridizes with the target nucleic acid sequence;

said method comprises: pre-adding in the amplification reaction solution a self-quenched probe, carrying out amplification under suitable reaction conditions, then performing melting curve analysis; analyzing whether a variation exists and, optionally, the type of variation based on the melting temperature of the hybrid formed between the self-quenched probe and the target nucleic acid, said reaction conditions are conditions assuring that after nucleic acid amplification, melting curve analysis can be performed with sufficient intact probes and sufficient single-stranded target sequences, preferably, said probe is a probe according to any one of paragraphs 1-17.

EXAMPLES

The present invention is further illustrated by the following examples in combination with the figures. What is provided are some specific examples of the present invention. These examples only serve to illustrate the invention rather than demonstrating all the possibilities of the present invention, and the present invention is not limited by the material, reaction conditions or parameters mentioned in these examples. Anyone with certain experience in the related field will be able to detect the genotype of single nucleotide variations as described in the present invention according to the principle of the present invention while using other similar materials or reaction conditions. These will not depart from the basic concepts described for the present invention.

Example 1

The Design of an Artificial Melting Temperature Tag Sequence (AMTS)

A fluorescent probe may hybridize with multiple different oligonucleotide sequences, but when hybridizing with different oligonucleotide sequences, different melting curve peaks will form, having different melting temperatures. The designed probes and target sequences are: Probe 1, Target 1, Target 2, Target 3, Target 4, Target 5, Target 6, Target 7, Target 8.

The reaction system of melting curve is: in 25 μL reaction solution, there were 2.5 μL 10×PCR buffer, 1.5 mM $MgCl_2$, 5 μmol probe 1, without a target sequence or with 10 μmol of one of the target sequences mentioned above. Carrying out melting curve analysis for the above mixture, the program of the reaction was: 95° C. denaturation for 1 min; maintaining at 35° C. for 2 min, then increasing the temperature from 40° C. to 90° C. with a rate of 1° C./step to perform the melting curve analysis, and collecting the fluorescence signal from the FAM channel.

This experiment was performed in a Rotor-gene 6000 real-time PCR machine.

Figure 1:
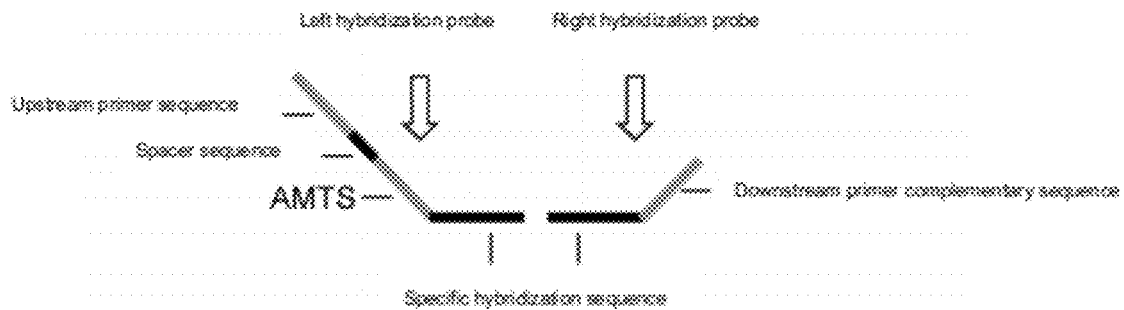
FIG. 1 shows the composition of a left hybridization ligation probe and a right hybridization ligation probe described in the present invention.
Figure 2:
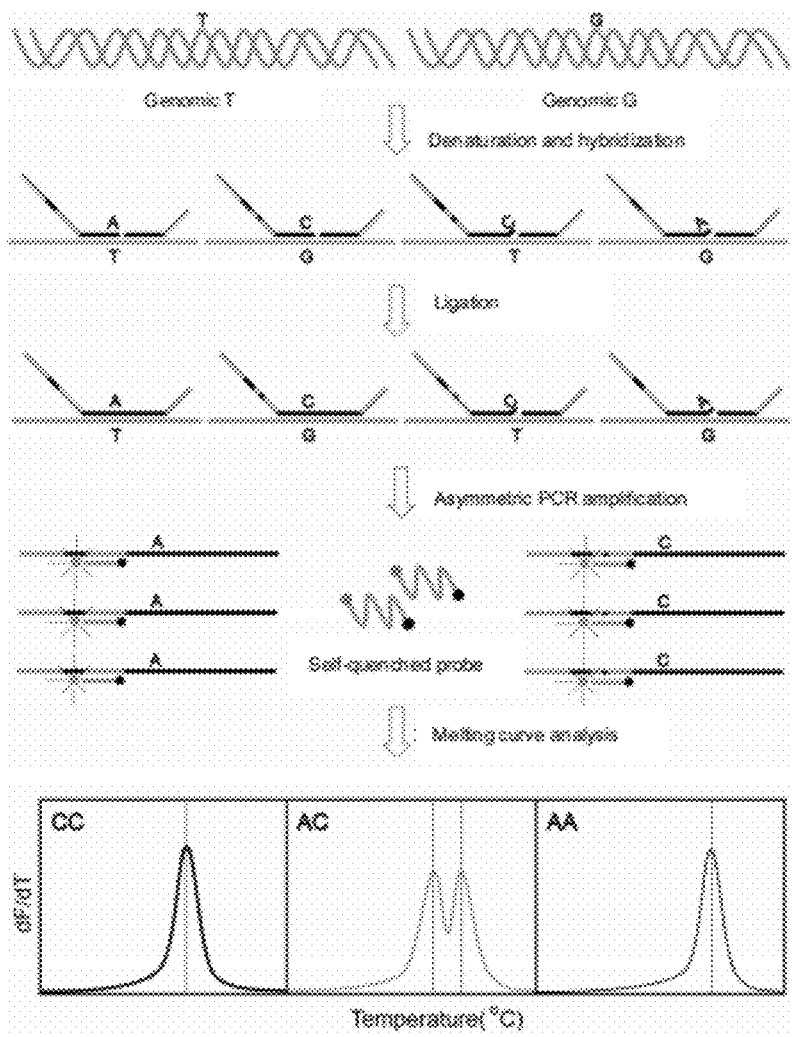
FIG. 2 illustrates the principle and steps of the present invention. It comprises from top to bottom: step 1: nucleic acid denaturation and probe hybridization; step 2: ligation reaction; step 3: PCR amplification; step 4: melting curve analysis, wherein the first step and the second step can be combined into one step, in addition, step 3 and step 4 may be carried out in the same reaction tube and can be incorporated into a single program.
Figure 3:
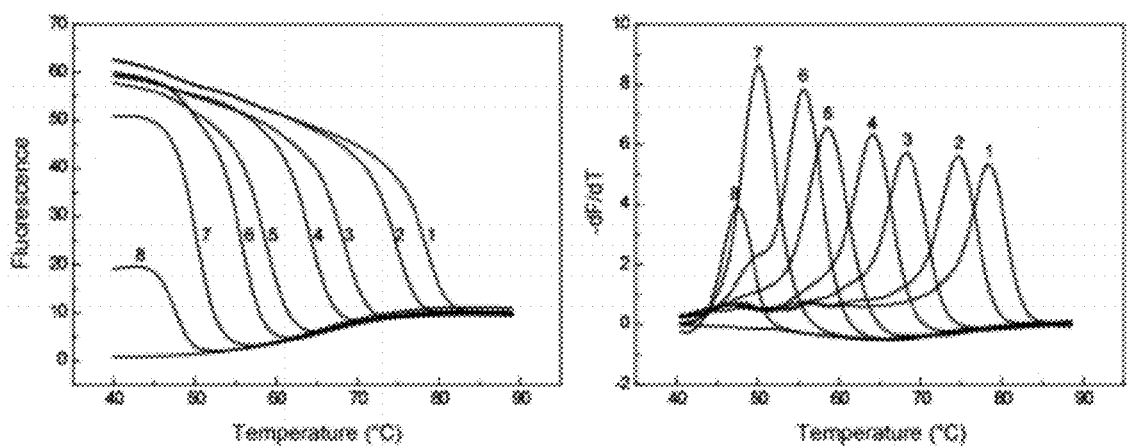
FIG. 3 shows the multiple different melting curve peaks formed upon the hybridization of one detection fluorescent probe with multiple AMTSs. The probes used in the figure are the probes of example 1, the numbers in the figure indicate the melting curves given by target sequences 1 to 8 of example 1. The left panel indicates the original melting curve and the right panel shows the melting curve peak after taking a derivation, the value of the peak corresponds to the melting temperature.

As shown by FIG. 3, one detection fluorescent probe can hybridize with multiple target sequences comprising mismatched bases, and thereby forming a gradient of multiple melting temperatures that can be differentiated from each other. Probe 1 of the present example formed at least 8 different melting temperature peaks with different target sequences. In the figure, the corresponding melting temperature of each melting curve peak are (from high to low): 78.32° C., 74.55° C., 68.21° C., 64.06° C., 58.62° C., 55.62° C., 50.11° C., 47.55° C. All of these target sequences can be used as an artificial melting temperature tag sequence.

Example 2

Detecting the Genotype of Single Nucleotide Variation Sites Through Two Different Melting Curve Peaks Taking the single nucleotide polymorphism site (SNP rs321198) as an example, designing two allele-specific left hybridization probes (SNPrs321198-1C and SNPrs321198-1T) and one general right hybridization probe (SNPrs321198-R) directing to the two homozygous genotypes C and T at this site, respectively, each allele-specific hybridization probe comprises a unique AMTS, the two AMTS can hybridize with a fluorescent probe (Probe 2), but the melting temperatures are different.

Based on this, genotypes can be determined according to the melting temperatures. The first base in the 5' end of the detection probe is modified with phosphorothioation, the bases in bold are replaced with a corresponding LNA.

The detection process comprises hybridization and ligation, PCR amplification and melting curve analysis, as specifically described below:

1) hybridization and ligation reaction: a 10 μL ligation reaction system is: 0.8 μL hybridization buffer (1.5 M KCl, 300 mM Tris-HCl pH 8.5, 1 mM EDTA), 0.1-1 nM hybridization probe, 1× Taq ligase buffer (20 mM Tris-HCl pH 7.6, 25 mM KAc, 10 mM $Mg(Ac)_2$, 10 mM DTT, 1 mM NAD, 0.1% Triton X-100), 1 U Taq ligase, 100 ng genomic DNA. Before adding the hybridization ligation reaction solution, the genomic DNA needs to be pre-denatured at 98° C. for 5 min. The program of hybridization ligation reaction is: 95° C. 1 min; 70° C. 2 min, 68° C. 2 min, 66° C. 2 min, 64° C. 2 min, 62° C. 2 min, 6 cycles.

2) PCR amplification and melting curve analysis: in 25 μL reaction system, there were 1 μL ligation product, 75 mmol/L Tris-HCl pH 9.0, 20 mmol/L $(NH_4)_2SO_4$, 0.01% Tween 20, 50 mmol/L KCl, 1 U Taq HS, 3 mmol/L $MgCl_2$, 0.2 μM Probe 2, 0.1 μM Primer-F, 2 μM Primer-R. The reaction program is: 95° C. 3 min; 95° C. 15 s, 55° C. 20 s, 75° C. 25 s, 50 cycles; 95° C. 1 min; 35° C. 5 min; then increasing the temperature from 40° C. to 80° C. with a rate of 1° C./step to perform the melting curve analysis, and collecting the fluorescence signal from the TET channel.

Figure 4:
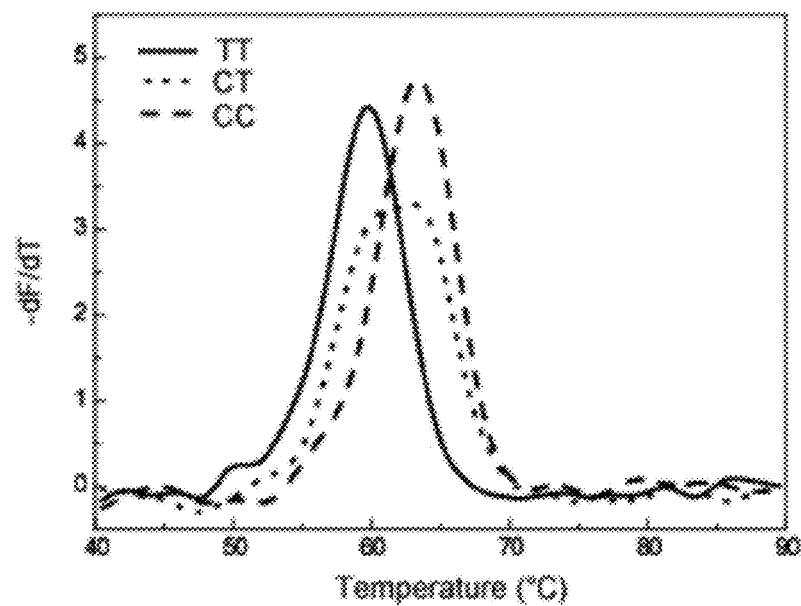
FIG. 4 shows that different homozygous genotypes of a single nucleotide polymorphism (SNPs) correspond to different melting curve peaks, respectively; and the heterozygous type shows another melting curve peak.

As shown in FIG. 4, the two homozygous genotypes correspond to the melting curve peaks of two unique Tm values; when the genotype is heterozygous, a specific fused peak will appear in the melting curve (when the Tm values of two homozygous genotypes only have minor differences, fusion will appear, and when the difference is relatively big, there will be two peaks). This example shows that distinguishing the genotypes of a SNP site can be achieved with different melting curve peaks.

Example 3

Detecting the Genotypes of a SNP Site from the Height of Melting Curve Peaks

Taking SNP (rs321198) as an example, for the two homozygous genotypes C and T of this SNP, only a left probe SNPrs321198-2C directing to the C type was designed, this probe comprised a unique AMTS, which hybridized with the fluorescent probe, probe 1. In addition, a competitive left probe SNPrs321198-3T was also designed for the T type, this probe was used in ligation and could amplify, but said probe does not comprise an AMTS, thus, the result of the melting curve analysis should be that the C type shows one melting curve peak, the heterozygous C and T show a low melting curve peak value at the same position, and the T type does not show any peak, the two probes share the same left probe SNPrs321198-R. Another site referred to as internal reference is used as a control for such changes of peak values, said internal reference site is a homozygous peak.

The hybridization and ligation reaction system is the same as in example 2, the differences are: besides the hybridization probes corresponding to SNPs, a pair of internal reference site (gene sequences not dependent on SNP) hybridization probes were also added into the ligation reaction system, said internal reference was meant to relatively quantify the height of the SNP melting curve peak of interest and thereby determining the genotype thereof. The system and programs for the PCR reaction and the melting analysis are the same as in example 2.

Figure 5:
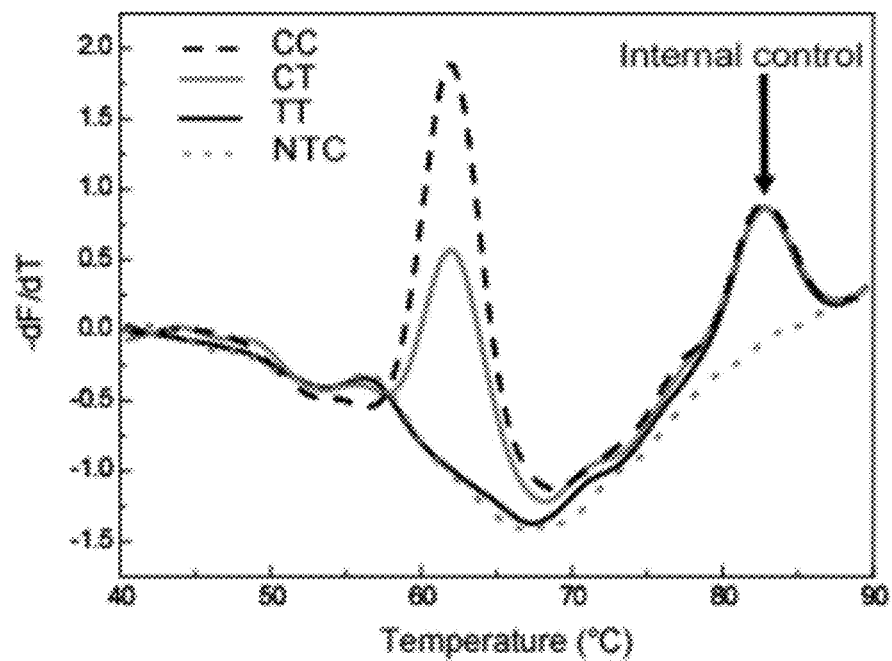
FIG. 5 illustrates the situation where a SNP site is detected with only one left ligation probe comprising AMTS, based on the internal reference peak, different genotypes of a SNP are differentiated using the height of melting curve peaks. In the figure, NTC represents negative template control reaction.

The results are shown in FIG. 5, under the condition that the height of the internal reference melting curve peaks is essentially consistent, the melting curve peak of homozygous CC is evidently higher than that of the heterozygous CT, while the homozygous TT does not show any melting curve peak at the position of said Tm. In the experiment, it was very difficult to ensure that the height of internal reference peaks is identical, however, we could solve this problem with a method of standardization (e.g. dividing the area of the melting curve peak of each specimen by the area of the melting curve peak of the corresponding internal reference).

Example 4

Adjusting the Height of Each Melting Curve Peak by Adjusting the Amount of Hybridization Probes Multiple different AMTSs can be detected with the same fluorescent probe, since every AMTS takes part in the competition for the fluorescent probe, leading to the fact that the corresponding melting curve peak of some less competitive AMTS is relatively low, which then affects genotyping of the SNPs. However, the height of each melting curve peak can be adjusted by adjusting the amount of hybridization probes. Taking the three AMTS, which all can hybridize with the fluorescent probe Probe 1 and have different melting temperatures, as examples (they correspond to the A type of SNP rs1109037, the C type of SNP rs321198 and the A type of SNP rs2076848, respectively) to illustrate that the height of each melting curve peak can be adjusted by adjusting the amount of hybridization probes. The sequence of the hybridization probes are SNPrs1109037-A, SNPrs1109037-R, SNPrs321198-2C, SNPrs321198-R, SNPrs2076848-A and SNPrs2076848-R.

The ligation reaction system is essentially identical to that of example 2, the differences are: in the ligation reaction system, the amount of the left probes added was adjusted from the initial ratio of 5 fmol: 5 fmol: 5 fmol to 2 fmol: 6 fmol: 10 fmol.

The system and program for the PCR reaction and the melting analysis were the same as in example 2.

Figure 6:
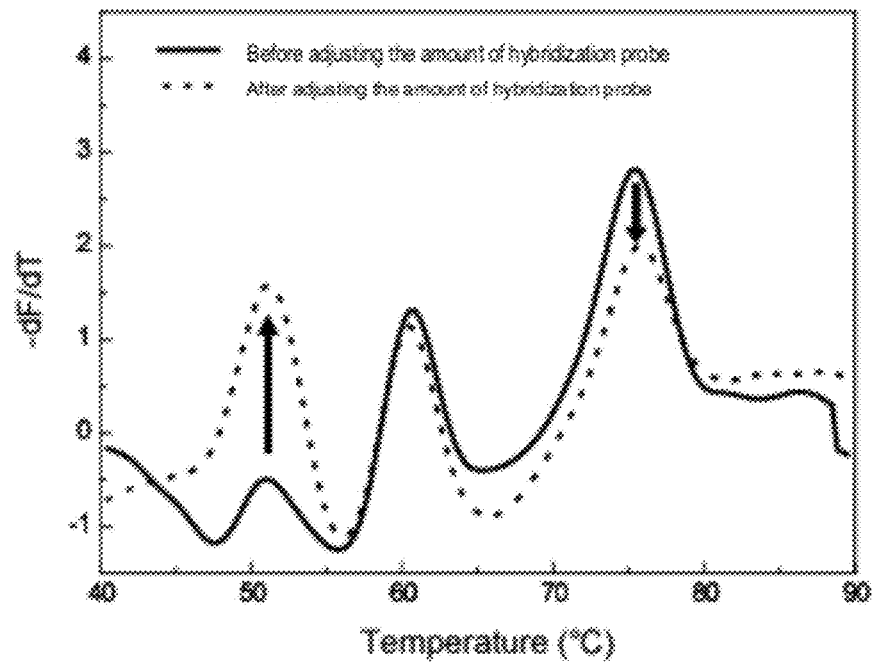
FIG. 6 demonstrates that the height of a melting curve peak may be adjusted by adjusting the amount of hybridization probes used.

The result is shown in FIG. 6, before adjusting the amount of hybridization probes, differences among the height of melting curve peaks corresponding to AMTS having different melting temperatures were relatively big, the overall tendency is that the AMTS having a high melting temperature corresponds to a relatively high peak, and the AMTS having a low melting temperature corresponds to a relatively low peak; however, after adjusting the amount of hybridization probes (i.e. increasing the amount of those hybridization probe pair corresponding to a relatively low peak, reducing the amount of those hybridization probe pair corresponding to a relatively low peak), and the height of melting curve peaks reached a relatively consistent level, which is advantageous for simultaneous detection of the genotype of multiple SNPs.

Example 5

Detecting the Genotype of Multiple SNPs in a Single Tube Using the Same Detection Fluorescent Probe The same detection fluorescent probe may hybridize with multiple AMTS, forming multiple different melting curve peaks, and thereby achieving the aim of simultaneously detecting the genotype of multiple SNPs in a single tube. Taking the detection of the genotype of 4 SNPs (rs1109037, rs321198, rs2076848, rs1523537) as an example, a corresponding set of hybridization probes were designed for each SNP, each of the allele-specific left hybridization probe comprises a unique AMTS, totally, there were 8 AMTS able to hybridize with the fluorescent probe (probe 1), but the corresponding melting temperatures were different. Thus, based on the final melting curve peak, one could determine the genotype of each SNP. The hybridization probe sequences used are SNPrs1109037-A, SNPrs1109037-G, SNPrs1109037-R, SNPrs321198-2C, SNPrs321198-2T, SNPrs321198-R, SNPrs2076848-A, SNPSNP-rs2076848-T, SNPrs2076848-R, SNPrs1523537-C, SNPrs1523537-T and SNPrs1523537-R.

Figure 7:
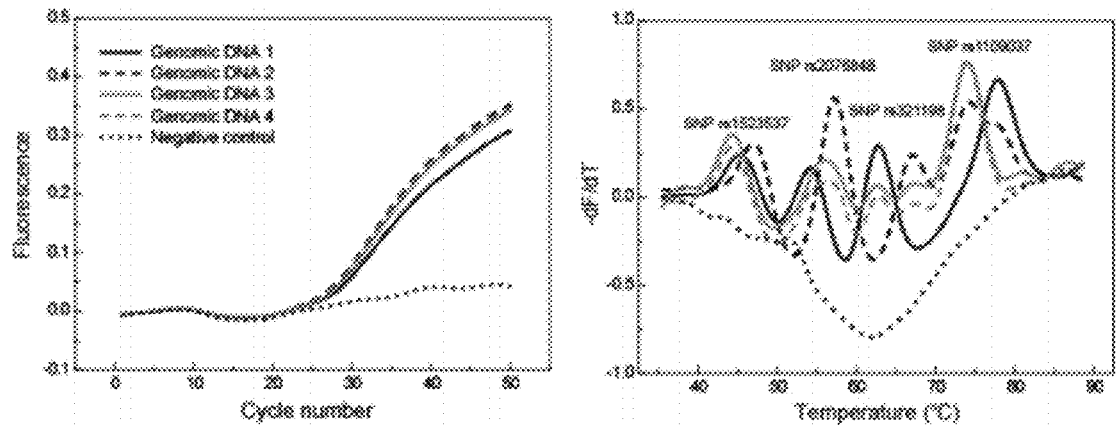
FIG. 7 illustrates that the genotype of multiple SNPs can be detected in a single tube using the same detection fluorescent probe. In this figure, the result of detecting the genotype of four SNP sites in the same reaction tube using one detection fluorescent probe is demonstrated. The left panel shows the real-time PCR curve, and the right panel shows the detection result of the melting curve of the present invention. Genotypes of the four SNPs in specimen 1 (Genomic DNA 1) are: AA(rs1109037), TT(rs321198), TT(rs2076848), CT(rs1523537); genotypes of the four SNPs in specimen 2 (Genomic DNA 2) are: AG(rs1109037), CC(rs321198), AA(rs2076848), CC(rs1523537); genotypes of the four SNPs in specimen 3 (Genomic DNA 3) are: GG(rs1109037), CT(rs321198), AT(rs2076848), TT(rs1523537); genotypes of the four SNPs in specimen 4 (Genomic DNA 4) are: GG (rs1109037), CT (rs321198), AT (rs2076848), TT (rs1523537).

The specific process of operation is the same as in example 2. Fluorescent signal from the FAM channel was collected during both the PCR amplification annealing stage and the melting curve analysis process. The result was shown in FIG. 7, for the specimens randomly examined (the genotype of their corresponding SNPs have been detected with a control method), in the real-time PCR amplification curve of each specimen, there were corresponding fluorescent signals arisen, but according to the arisen fluorescent signals of real-time PCR, the genotype of the various SNP sites in the specimens cannot be determined. With the melting curve analysis after PCR, the genotype of each SNP site could be relatively directly obtained from its corresponding melting curve peak.

Example 6

Detecting the Genotype of Multiple SNPs in a Single Tube Using Multiple Different Detection Fluorescent Probes Simultaneous detection of the genotype of multiple SNPs in a single tube can be achieved using the same detection fluorescent probe; simultaneous detection of the genotype of more SNPs in a single tube can be achieved with multiple detection fluorescent probes labeled with multiple different colors. Taking two SNPs (rs1109037 and rs321198) as an example, corresponding hybridization probes were designed directing to these two SNPs, wherein the hybridization probe corresponding to SNP rs1109037 comprises an AMTS able to hybridize with the detection fluorescent probe Probe 1, the hybridization probe corresponding to SNP rs321198 comprises an AMTS able to hybridize with the detection fluorescent probe Probe 2, thus, based on the melting curve peaks of different detection fluorescent probes, one could determine the genotype of different SNPs. The sequences of the hybridization probes used are: SNPrs1109037-A, SNPrs1109037-G, SNPrs1109037-R, SNPrs321198-1C, SNPrs321198-1T: 5, SNPrs321198-R.

The hybridization and ligation reaction, the system and program of PCR amplification and melting analysis were all the same as in example 2. In the system of PCR and melting analysis, two detection fluorescent probes (Probe 1 and Probe 2) were added, respectively labeled with a FAM or a TET fluorescent group. During the PCR amplification reaction and the melting curve analysis, fluorescent signals from the FAM and TET channels were collected.

Figure 8:
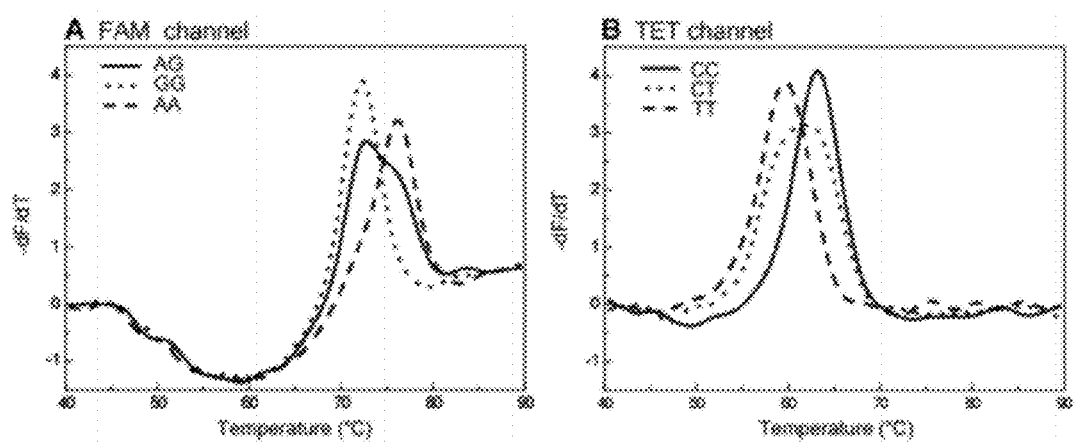
FIG. 8 demonstrates that the genotype of multiple SNPs can be detected in a single tube using two fluorescently labeled detection fluorescent probes. The left panel shows the result of detecting a FAM-labeled fluorescent probe with a FAM Channel; the right panel shows the result of detecting a TET-labeled fluorescent probe with a TET Channel.

The results were shown in FIG. 8, in the FAM channel, different genotypes of SNP (rs321198) have their respectively corresponding melting curve peaks; in the TET channel, different genotypes of SNP (rs7520386) also have their respectively corresponding melting curve peaks. This example demonstrates that by using detection fluorescent probes labeled with different colors, detection of multiple different SNPs in a single tube can be achieved. In combination with the fact that the genotype of multiple SNPs can be detected in a single tube with the same probe, in a multi-channel detection PCR machine (4-6 colors), simultaneous detection of multiple SNPs can be achieved by using multiple detection fluorescent probes labeled with different colors.

Example 7

Detecting the Genotype of 48 Human Genomic SNPs Using a Four-Color AMTS Fluorescent Probe In this example, we detected 48 human genomic SNPs using multi-color fluorescence labels. The two allelic homozygous genotypes of each SNP site were respectively labeled with two AMTS labels, the 8 AMTS tags of four SNPs were detected using one fluorescently labeled probe. In this way, the genotype of 16 SNPs can be detected using four fluorescent probes. The whole process comprises: putting all the probes in the same reaction tube (for each SNP, the number of probes in a hybridization and ligation probe set was 3, i.e. two left probes and 1 right probe; thus, there were totally 144 probes for 48 SNP sites); after hybridization and ligation, the products were distributed into 3 PCR amplification systems to be amplified, said amplification system comprises 4 self-quenched probes, respectively labeled with FAM, ROX, CAL(CAL Fluor® Red 635) or TET; these four probes were commonly used in every amplification reaction tubes and the reaction systems were identical, but the primers were different, as described below:

1) hybridization and ligation reaction: a 10 μL ligation reaction system was: 2-20 fM hybridization probe, 1×0.8 μL Taq ligase buffer (20 mM Tris-HCl pH 7.6, 25 mM KAc, 10 mM Mg(Ac)$_2$, 10 mM DTT, 1 mM NAD, 0.1% Triton X-100), 1 U Taq ligase, 100 ng genomic DNA. Before adding the hybridization ligation reaction solution, the mixture of genomic DNA and hybridization probes needs to be pre-denatured at 98° C. for 5 min. The program of hybridization ligation reaction was: 95° C. 2 min; 66° C. 2 min, 64° C. 2 min, 62° C. 2 min, 60° C. 2 min, 58° C. 2 min, 6 cycles.

Figure 9:
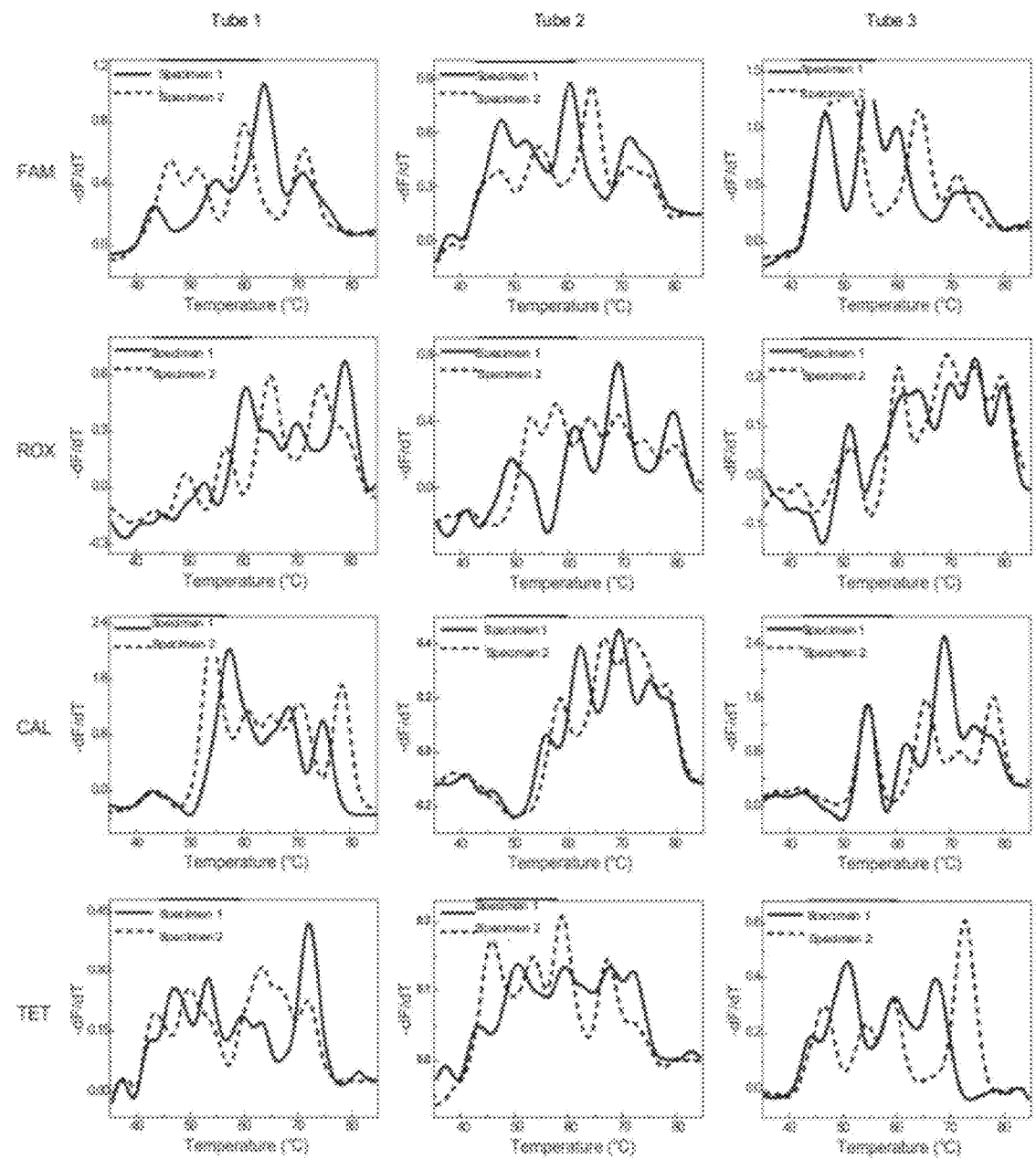
FIG. 9 shows that the genotypes of 48 human genomic SNPs are detected with four-color AMTS fluorescent probes.

2) PCR amplification and melting curve analysis: in 25 μL reaction system, there were 1 μL ligation products, 75 mM Tris-HCl pH 9.0, 20 mM (NH$_4$)$_2$SO$_4$, 0.01% Tween 20, 50 mM KCl, 1 U Taq HS, 3 mM MgCl$_2$, 0.12 μM Primer-F, 1.2 μM Primer-R, FAM channel hybridization probe 0.25 μM, ROX, CAL (CAL Fluor® Red 635), TET channel hybridization probe 0.2 μM. The reaction program was: 95° C. 3 min; 95° C. 5 s, 55° C. 10 s, 75° C. 15 s, 50 cycles; 95° C. 1 min; 35° C. 5 min; then increasing the temperature from 35° C. to 89° C. with a rate of 1° C./step to perform the melting curve analysis, and collecting the fluorescent signal from corresponding channels. FIG. 9 shows the analysis result for the genotype of two human genomic SNP specimens, based on the melting temperatures set beforehand, the genotypes of 48 SNPs in the two specimens are listed in table 1.

Example 8

Detecting 9 Mutated Genotypes of G6PD Deficiency Using a Tri-Color AMTS Probe In this example, 9 common point mutations causing G6PD deficiency in Chinese people were detected in a single tube using multiple different detection fluorescent probes.

Figure 10:
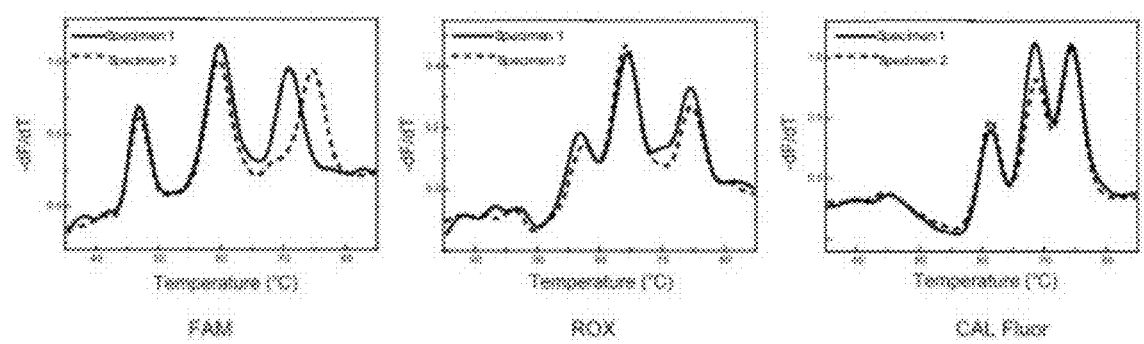
FIG. 10 shows that 9 mutated genotypes of G6PD deficiency are detected with tricolor AMTS fluorescent probes.

In this example, we detected 9 common point mutations causing G6PD deficiency in Chinese people using a tricolor fluorescence label. The principle of design is the same as for detecting SNPs. The two allelic homozygous genotypes of each mutated site were respectively labeled with two AMTS labels, the 6 AMTS tags of three mutated sites were detected using one fluorescently labeled probe. In this way, the genotype of 9 mutated sites can be detected using three fluorescent probes. The whole process comprises: putting all the probes in the same reaction tube (for each mutated site, the number of probes in a hybridization and ligation probe set was 3, i.e. two left probes and 1 right probe; thus, there were totally 27 probes for 9 mutated sites); after hybridization and ligation, the products were amplified in a tricolor PCR amplification system, said amplification system comprises 3 self-quenched probes, respectively labeled with FAM, ROX or CAL (CAL Fluor® Red 635). The specific process is the same as in example 7. FIG. 10 shows the detection result for the mutated genotypes in the two specimens, based on the melting temperatures set beforehand, the genotypes are listed in table 2.

TABLE 1

Detection results for 48 SNPs in two human genomic specimens

| Type of fluorescent labels | Amplification reaction tube 1 | | | | | | | | Amplification reaction tube 2 | | | | Amplification reaction tube 3 | | | |
|---|---|---|---|---|---|---|---|---|---|---|---|---|---|---|---|---|
| | Detection results for 48 SNPs in specimen 1 | | | | | | | | | | | | | | | |
| FAM | CT | AA | CC | TT | AG | GG | TT | AA | AG | TT | CC | CC | | | | |
| ROX | AA | AT | AA | CT | CC | AA | AA | AT | CT | CT | CT | CC | | | | |
| CAL | GG | TT | AC | AA | AG | GG | GG | GG | CT | TT | CC | TT | | | | |
| TET | CC | AG | AA | GC | CT | CT | TT | CC | GG | AG | GG | TT | | | | |
| | Detection results for 48 SNPs in specimen 2 | | | | | | | | | | | | | | | |
| FAM | TT | GG | TT | CC | AG | AA | AA | AT | GG | CC | GG | CC | | | | |
| ROX | AG | TT | GG | TT | CG | AG | GG | AA | CT | CC | CC | CT | | | | |
| CAL | CC | GG | AC | CC | AG | CC | CC | AA | CC | CC | TT | TT | | | | |
| TET | CT | AA | AT | CC | TT | TT | CC | TT | AA | GG | AA | CC | | | | |

TABLE 2

Detection results for the 9 mutations in G6PD deficiency

| Type of fluorescent labels | Genotype of the mutated sites | | |
|---|---|---|---|
| FAM | 1414A > C | 1360C > T | 1376G > T |
| | Specimen1: wild type AA | Specimen1: wild type CC | Specimen1: wild type GG |
| | Specimen 2: wild type AA | Specimen 2: wild type CC | Specimen 2: mutated type TT |
| ROX | 202G > A | 592C > T: | 487G > A |
| | Specimen 1: wild type GG | Specimen 1: wild type CC | Specimen 1: wild type GG |
| | Specimen 2: wild type GG | Specimen 2: wild type CC | Specimen 2: wild type GG |

TABLE 2-continued

Detection results for the 9 mutations in G6PD deficiency

| Type of fluorescent labels | Genotype of the mutated sites | | |
|---|---|---|---|
| CAL | 835A > T<br>Specimen 1: wild type AA<br>Specimen 2: wild type AA | 871G > A<br>Specimen 1: wild type GG<br>Specimen 2: wild type GG | 1024C > T<br>Specimen 1: wild type CC<br>Specimen 2: wild type CC |

Sequences Used in the Examples

| Name of the sequences | Sequence (5'→3') | SEQ ID NO |
|---|---|---|
| Probe 1 | FAM-CCGGTCCTTCATCGCTCAGCCTTCACCGG-BHQ | 1 |
| Target 1 | TTTTTCCGGTGAAGGCTGAGCGATGAAGGACCTTTTT | 2 |
| Target 2 | TTTTTCCGGTGATGGCTGAGCGATGAAGGACCTTTTT | 3 |
| Target 3 | TTTTTCCGGTGATGGCTGAGCGATTAAGGACCTTTTT | 4 |
| Target 4 | TTTTTCCGGTGAAGCCTGAGCGATTAAGGACCTTTTT | 5 |
| Target 5 | TTTTTCCGGTGATGGCTGACCGATCAAGGACCTTTTT | 6 |
| Target 6 | TTTTTCCGGTCAAGGTTGAGTTATGAAGGACCTTTTT | 7 |
| Target 7 | TTTTTCCGGTGTAGGTTCAGAGATCAAGGACCTTTTT | 8 |
| Target 8 | TTTTTCCGGTGTAGGTTGAGACATCAAGGACCTTTTT | 9 |
| SNPrs32 1198-1C | TGGGTTCCCTAAGGGTTGGACCTCACTCAGTTCAGTTATATGGATGATGTGGCTGTTTTCCTTTTGTGATTCCACTTCC | 10 |
| SNPrs32 1198-1T | TGGGTTCCCTAAGGGTTGGACCTCACTCAGTTCAGCTATATGGATGATGTGGCCTGTTTTCCTTTTGTGATTCCACTTCT | 11 |
| SNPrs32 1198-R | PO$_4$-GTGTGAAGCAAGCAGTGCTTGTTT-TAA<br>TCAGTCTAGATTGGATCTTGCTGGCAC | 12 |
| Primer-F | TGGGTTCCCTAAGGGTTGGA | 13 |
| Primer-R | GTGCCAGCAAGATCCAATCTAGA | 14 |
| Probe 2 | TET-TTCAGTTATATGGATGATGTGG-BHQ | 15 |
| SNPrs32 1198-2C | TGGGTTCCCTAAGGGTTGGACGTCACTCAGGGTCCTTAATCGCTCAGCCATCACCGGCTGTTTTCCTTTTGTGATTCCACTTCC | 16 |
| SNPrs32 1198-3T | TGGGTTCCCTAAGGGTTGGACGTCACTCAGCCTGTTTTCCTTTTGTGATTCCACTTCT | 17 |
| SNPrs32 1198-R | PO$_4$-GTGTGAAGCAAGCAGTGCTTGTTT-TAA<br>TCAGTCTAGATTGGATCTTGCTGGCAC | 18 |
| SNPrs11 09037-A | TGGGTTCCCTAAGGGTTGGACGTCACTCAGGGTCCTTCATCGCTCAGCCTTCACCGGCCTCCCACACCAGTTTCTCCA | 19 |
| SNPrs11 09037-R | PO$_4$-GAGTGGAAAGACTTTCATCTCG-CACTG<br>GTCTAGATTGGATCTTGCTGGCAC | 20 |
| SNPrs32 1198-2C | TGGGTTCCCTAAGGGTTGGACGTCACTCAGGGTCCTTAATCGCTCAGCCATCACCGGCTGTTTTCCTTTTGTGATTCCACTTCC | 21 |
| SNPrs32 1198-R | PO$_4$-GTGTGAAGCAAGCAGTGCTTGTTT-TAA<br>TCAGTCTAGATTGGATCTTGCTGGCAC | 22 |
| SNPrs20 76848-A | TGGGTTCCCTAAGGGTTGGACGTCACTCAGGGTCCTTGATCGCTCAGCCATCACCGGCTCACCACCAGAAATCAGGGCA | 23 |
| SNPrs20 76848-R | PO$_4$-TGATGGACCTGAAGCGGTCCCGTCTA<br>GATTGGATCTTGCTGGCAC | 24 |
| SN Prs11 09037-A | TGGGTTCCCTAAGGGTTGGACGTCACTCAGGGTCCTTCATCGCTCAGCCTTCACCGGCCTCCCACACCAGTTTCTCCA-3' | 25 |
| SNPrs11 09037-G | TGGGTTCCCTAAGGGTTGGACGTCACTCAGGGTCCTTCATCGCTCAGCCATCACCGGCCTCCCACACCAGTTTCTCCG-3' | 26 |
| SNPrs11 09037-R: | PO$_4$-GAGTGGAAAGACTTTCATCTCG-CACTG<br>GTCTAGATTGGATCTTGCTGGCAC-3' | 27 |
| SNPrs32 1198-2C | TGGGTTCCCTAAGGGTTGGACGTCACTCAGGGTCCTTAATCGCTCAGCCATCACCGGCTGTTTTCCTTTTGTGATTCCACTTCC3' | 28 |
| SNPrs32 1198-2T: | TGGGTTCCCTAAGGGTTGGACGTCACTCAGGGTCCTTAATCGCTCAGGCTTCACCGGCCTGTTTTCCTTTTGTGATTCCACTTCT3' | 29 |
| SNPrs32 1198-R | PO$_4$-GTGTGAAGCAAGCAGTGCTTGTTT-TAA<br>TCAGTCTAGATTGGATCTTGCTGGCAC-3' | 30 |
| SNPrs20 76848-A | TGGGTTCCCTAAGGGTTGGACGTCACTCAGGGTCCTTGATCGGTCAGCCATCACCGGCTCACCACCAGAAATCAGGGCA-3' | 31 |
| SNPSNP-rs2076848-T | TGGGTTCCCTAAGGGTTGGACGTCACTCAGGGTCCTTCATAACTCAACCTTGACCGGCTCACCACCAGAAATCAGGGCT-3' | 32 |
| 2076848-R | PO$_4$-TGATGGACCTGAAGCGGTCCCGTCTA<br>GATTGGATCTTGCTGGCAC | 33 |
| SNPrs15 23537-C | TGGGTTCCCTAAGGGTTGGACGTCACTCAGGGTCCTTGATCTCTGAACCTACACCGGCAGTCTGCAACAAGATCTTGTAGGGAC | 34 |
| SNPrs15 23537-T | TGGGTTCCCTAAGGGTTGGACGTCACTCAGGGTCCTTGTTCTCTGAACCTTCACCGGCAGTCTGCAACAAGATCTTGTAGGGAT | 35 |
| SNPrs15 23537-R | PO$_4$-GCTATCGCTGGCTATTAGGTGAT-CACA<br>GTTCTGTCTAGATTGGATCTTGCTGGCAC | 36 |
| SNPrs11 09037-A | TGGGTTCCCTAAGGGTTGGACGTCACTCAGGGTCCTTCATCGCTCAGCCTTCACCGGCCTCCCACACCAGTTTCTCCA | 37 |

| Name of the sequences | Sequence (5'→3') | SEQ ID NO |
|---|---|---|
| SNPrs11 09037-G | TGGGTTCCCTAAGGGTTGGACGTCACTCA GGGTCCTTCATCGCTCAGCCATCACCGGC CTCCCACACCAGTTTCTCCG | 38 |
| SNPrs11 09037-R | PO$_4$-GAGTGGAAAGACTTTCATCTCG-CACTG GTCTAGATTGGATCTTGCTGGCAC | 39 |
| SNPrs32 1198-1C | TGGGTTCCCTAAGGGTTGGACCTCACTCA GTTCAGTTATATGGATGATGTGGCTGTTTT CCTTTTGTGATTCCACTTCC | 40 |
| SNPrs32 1198-1T | TGGGTTCCCTAAGGGTTGGACCTCACTCA GTTCAGCTATATGGATGATGTGGCCTGTTT TCCTTTTGTGATTCCACTTCT | 41 |
| SNPrs32 1198-R | PO$_4$-GTGTGAAGCAAGCAGTGCTTGTTT-TAA TCAGTCTAGATTGGATCTTGCTGGCAC | 42 |

REFERENCES

1. Ragoussis, J. Annual Review of Genomics and Human Genetics, 2009, 10, 117-133
2. Livak, K. J. Genetic Analysis, 1999, 14, 143-149.
3. Afonina, I. A. et al, Biotechniques, 2002, 32, 4, 940-944, 946-949.
4. Tyagi, S. et al, Nature Biotechnology, 1998, 16, 49-53.
5. Li, Q., et al, Nucleic Acids Research, 2002, 30, E5.
6. Whitcombe, D. et al, Nature Biotechnology, 1999, 17, 804-807.
7. Nazarenko, I. A., et al, Nucleic Acids Research, 1997, 25, 1516-1521.
8. Ruan L, et al. Transfusion. 2007, 47(9):1637-42.
9. Nicklas J A, et al. Journal of Forensic Sciences, 2008, 53(6):1316-24.
10. Li Qingge, Chinese patent application No. 200910143480.6
11. Bernard, P. S., et al, American Journal of Pathology, 1998, 153, 1055-1061.
12. El-Hai Hiyam H. et al, Journal of Clinical Microbiology, 2009, 47, 4, 1190-1198.
13. French, D. J., et al, Molecular and Cellular Probes, 2001. 15, 363-374.
14. Gupta, A. P. et al, US patent application, US 2007/0020664 A10.

What is claimed:

1. A method for detecting single nucleotide polymorphisms (SNPs) at least at a first site and a second site in a template DNA in a single reaction tube, comprising:

(1) providing, in a single reaction tube:

(A) at least a first pair of hybridization probes and a second pair of hybridization probes, wherein:

(i) the first pair of hybridization probes comprises: (a) a first left hybridization probe which comprises, from its 5' end to its 3' end, a universal upstream primer binding sequence, a spacer sequence, a first artificial melting temperature tag sequence (AMTS) specific for the genotype of a first single nucleotide polymorphism (SNP) at the first site in the template DNA, and a first template hybridization sequence, wherein the base at the 3' end of the first left hybridization probe is complementary to the nucleotide of the first SNP at the first site in the template DNA; and (b) a first right hybridization probe which comprises, from its 5' end to its 3' end, a second template binding sequence and a universal downstream primer binding sequence, wherein the first left hybridization probe and the first right hybridization probe are adjacent to each other on the template DNA after they hybridize to the template DNA and are capable of being ligated to each other on the template DNA by a DNA ligase; and (ii) the second pair of hybridization probes comprises: (a) a second left hybridization probe which comprises, from its 5' end to its 3' end, a universal upstream primer binding sequence, a spacer sequence, a second AMTS sequence specific for the genotype of a second SNP at the second site in the template DNA, and a third template hybridization sequence, wherein the base at the 3' end of the second left hybridization probe is complementary to the nucleotide of the second SNP; and (b) a second right hybridization probe which comprises, from its 5' end to its 3' end, a fourth template binding sequence and the universal downstream primer binding sequence, wherein the second left hybridization probe and the second right hybridization probe are adjacent to each other on the template DNA after they hybridize to the template DNA and are capable of being ligated to each other on the template DNA by a DNA ligase, wherein the first site and the second site are located on different locations of the template DNA;

(B) denatured template DNA;

(C) a hybridization buffer;

(D) a ligase; and (E) a ligation buffer;

(2) performing hybridization and ligation reactions in the single reaction tube, thereby forming (a) a first complete single-stranded nucleic acid comprising the first left hybridization probe and the first right hybridization probe and (b) a second complete single-stranded nucleic acid comprising the second left hybridization probe and the second right hybridization probe;

(3) performing a polymerase chain reaction (PCR) in the single reaction tube using a pair of universal primers, wherein the pair comprises (a) a universal upstream primer that hybridizes with the universal upstream primer sequence, and (b) a universal downstream primer that hybridizes with the universal downstream primer binding sequence, thereby producing the first complete single-stranded nucleic acid and the second complete single-stranded nucleic acid, wherein the first complete single-stranded nucleic acid comprises the first AMTS and the second complete single-stranded nucleic acid comprises the second AMTS;

(4) forming a first duplex and a second duplex by either (i) performing the PCR in the presence of a fluorescent probe which is capable of hybridizing with the first AMTS and the second AMTS or (ii) adding the fluorescent probe into the single reaction tube after the PCR, wherein the first duplex comprises the first AMTS and the first fluorescent probe and wherein the second duplex comprises the second AMTS and the second fluorescent probe; and (5) generating fluorescent melting curves of the first duplex and the second duplex and performing melting curve analysis on the first duplex and the second duplex, thereby detecting the first SNP at the first site in the template DNA and the second SNP at the second site in the template DNA based on the heights of the melting curve peaks of the fluorescent melting curves of the first duplex and the second duplex.

2. The method of claim 1, wherein the fluorescent probe is a self-quenched probe.

3. The method of claim 1, wherein the first duplex and the second duplex are formed by performing the PCR in the presence of the fluorescent probe.

4. The method of claim 1, wherein the first duplex and a second duplex are formed by adding the fluorescent probe into the first and second fluorescent probes are added to the single reaction tube after the PCR.

* * * * *